US012797404B2

(12) United States Patent
Li et al.

(10) Patent No.: US 12,797,404 B2
(45) Date of Patent: Nov. 17, 2026

(54) CELLULAR IMMUNOTHERAPY IN COMBINATION WITH GEMCITABINE

(71) Applicant: CRAGE medical Co., Limited, Hong Kong (CN)

(72) Inventors: Zonghai Li, Shanghai (CN); Xiuqi Wu, Shanghai (CN)

(73) Assignee: CRAGE MEDICAL CO., LIMITED, Hong Kong (CN)

(*) Notice: Subject to any disclaimer, the term of this patent is extended or adjusted under 35 U.S.C. 154(b) by 1391 days.

(21) Appl. No.: 17/421,133

(22) PCT Filed: Jan. 7, 2020

(86) PCT No.: PCT/CN2020/070717

§ 371 (c)(1),
(2) Date: Jan. 31, 2022

(87) PCT Pub. No.: WO2020/143631

PCT Pub. Date: Jul. 16, 2020

(65) Prior Publication Data

US 2022/0152101 A1 May 19, 2022

(30) Foreign Application Priority Data

Jan. 7, 2019 (CN) ......................... 201910012164.9

(51) Int. Cl.

| | |
|---|---|
| ***A61K 35/17*** | (2025.01) |
| ***A61K 31/7068*** | (2006.01) |
| ***A61K 38/17*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |

(52) U.S. Cl.

CPC ...... *A61K 31/7068* (2013.01); *A61K 38/1774* (2013.01); *A61K 40/11* (2025.01); *A61K 40/31* (2025.01); *A61K 40/4202* (2025.01); *A61P 35/00* (2018.01); *A61K 2239/31* (2023.05); *A61K 2239/38* (2023.05); *A61K 2239/54* (2023.05)

(58) Field of Classification Search

CPC ...................... A61K 31/7068; A61K 38/1774; A61K 40/11; A61K 40/31; A61K 2239/38; A61K 35/17; A61P 35/00; C07K 14/7051; C07K 2317/622; C07K 2319/00; C07K 16/28

See application file for complete search history.

(56) References Cited

U.S. PATENT DOCUMENTS

| | | | | |
|---|---|---|---|---|
| 10,093,736 B2 * | 10/2018 | Sahin | ................. | C07K 16/2809 |
| 10,377,822 B2 * | 8/2019 | Wang | ..................... | A61K 35/17 |
| 2017/0334991 A1 | 11/2017 | Escarpe et al. | | |
| 2018/0282389 A1 | 10/2018 | Sahin et al. | | |

FOREIGN PATENT DOCUMENTS

| | | | |
|---|---|---|---|
| CN | 107058354 | 8/2017 | |
| CN | 107207580 | 9/2017 | |
| CN | 107960056 | 4/2018 | |
| CN | 108853144 | 11/2018 | |
| CN | 108853144 A * | 11/2018 | ......... A61K 40/4204 |
| EP | 3 483 182 | 5/2024 | |
| JP | 2016-510721 | 4/2016 | |
| JP | 2017-535283 | 11/2017 | |
| JP | 2018-509459 | 4/2018 | |
| WO | 2014/127906 | 8/2014 | |
| WO | 2016/073649 | 5/2016 | |
| WO | 2016/160621 | 10/2016 | |
| WO | 2016/180782 | 11/2016 | |
| WO | 2018/006882 | 1/2018 | |
| WO | 2018/063985 | 4/2018 | |

OTHER PUBLICATIONS

Bunt, S.K., 2013. Rosiglitazone and Gemcitabine in combination reduces immune suppression and modulates T cell populations in pancreatic cancer. Cancer immunology, immunotherapy, 62(2), pp. 225-236. (Year: 2013).*

Extended European Search Report issued Oct. 13, 2022 in corresponding European Patent Application No. 20738673.1, 10 pages.

Fuca et al., "Enhancing Chimeric Antigen Receptor T Cell Efficacy in Solid Tumors", Clinical Cancer Research, 2020, vol. 26, No. 11, pp. 2444-2451, 31 pages.

Martinez et al., "CAR T cells for Solid Tumors: New Strategies for Finding, Infiltrating, and Surviving in the Tumor Microenvironment", Frontiers in Immunology, 2019, vol. 10, 33 pages.

Gebremeskel et al., "Natural killer T-cell immunotherapy in combination with chemotherapy-induced immunogenic cell death targets metastatic breast cancer", Cancer Immunology Research, 2017, vol. 5, No. 12, pp. 1086-1097, 41 pages.

Sasso et al., "Low dose gemcitabine-loaded lipid nanocapsules target monocytic myeloid-derived suppressor cells and potentiate cancer immunotherapy", Biomaterials, 2016, vol. 96, , pp. 47-62, 37 pages.

International Search Report issued Apr. 8, 2020 in International (PCT) Application No. PCT/CN2020/070717, 5 pages.

(Continued)

*Primary Examiner* — Jeremy C Flinders
*Assistant Examiner* — Masudur Rahman
(74) *Attorney, Agent, or Firm* — Wenderoth, Lind & Ponack, L.L.P.

(57) ABSTRACT

Disclosed is a tumor treatment method, wherein immune effector cells and Gemcitabine are administered to an individual with tumor, and the immune effector cells express receptors having a tumor-specific antigen. Also disclosed is a tumor treatment kit, wherein the kit comprises 1) immune effector cells expressing receptors that recognize tumor antigens; 2) Gemcitabine; 3) a container for containing the substances of 1) and 2) described above; and 4) drug administration instructions for using the kit to treat a tumor.

13 Claims, 4 Drawing Sheets

Specification includes a Sequence Listing.

(56) References Cited

OTHER PUBLICATIONS

Aoki et al., "Adjuvant combination therapy with gemcitabine and autologous γ δ T-cell transfer in patients with curatively resected pancreatic cancer", Cytotherpy, 2017, vol. 19, No. 4, pp. 473-485, 13 pages.
Enblad, et al., "CAR T-Cell Therapy: The Role of Physical Barriers and Immunosuppression in Lymphoma", Human Gene Therapy, 2015, vol. 26, No. 8, pp. 498-505, 8 pages.
Yuan et al., "Phase II Clinical Trial of Chemotherapy Combined with Autologous CIK Cells Transfusion in the Treatment for Metastatic Renal Cell Carcinoma", Journal of Chinese Oncology, 2008, vol. 14, No. 5, pp. 362-365, 5 pages.
Yu et al., "Gemcitabine in combination with dendritic cell-induced immuneeffector cells inhibits the growth of BxPC-3 cells", World Chinese Journal of Digestology, 2010, vol. 18, No. 20, pp. 2095-2101, 8 pages.
Extended Search Report issued Oct. 13, 2022, in corresponding European Patent Application No. 20738673.1.
Deselm Carl J. et al: "CAR T-cell therapy for pancreatic cancer", Journal of Surgical Oncology, vol. 116, No. 1, Mar. 27, 2017, pp. 63-74.
E. Suzuki: "Gemcitabine Selectively Eliminates Splenic Gr-1+/CD11b+ Myeloid Suppressor Cells in Tumor-Bearing. Animals and Enhances Antitumor Immune Activity", Clinical Cancer Research, vol. 11, No. 18, Sep. 15, 2005, pp. 6713-6721.
Ma Qiujuan, "Patent Prospects for Precision Medicine", Intellectual Property Press, p. 52, Sep. 30, 2018.
Chen Jie et al., Clinical Drug Quick Reference Handbook, 3rd Edition, Guangdong Science and Technology Press, p. 456, Mar. 31, 2018.
Chinese Decision of Rejection issued Apr. 10, 2025, in corresponding Chinese Patent Application No. 202504100139880, with English translation.
Japanese Office Action issued Nov. 18, 2022, in corresponding Japanese Patent Application No. 2021-539884, with English translation.

* cited by examiner

CELLULAR IMMUNOTHERAPY IN COMBINATION WITH GEMCITABINE

FIELD OF THE INVENTION

This application belongs to the field of cellular immunotherapy, and particularly relates to a combination of an immune effector cell and Gemcitabine for anti-tumor therapy.

BACKGROUND OF THE INVENTION

In recent years, cellular immunotherapy, such as CAR-T cell therapy, has shown amazing therapeutic effects in the treatment of hematologic tumor. At present, more than 200 CAR-T cell clinical trials have been used in the treatment of hematologic tumor (Clinical development of CAR T cells-challenges and opportunities in translating innovative treatment concepts, Jessica Hartmann et al., EMBO Molecule Medicine, Published on line, Aug. 1, 2017). However, the treatment effect of solid tumors is difficult to achieve that of the hematologic tumor treatment.

This is because for hematologic tumors, CAR-T cells can more easily reach tumor cells through intravenous infusion to achieve killing, while it is more difficult for homing of CAR-T cells to the tumor tissue of solid tumors. In addition, solid tumors usually have a complex and dynamic tumor microenvironment that can make tumor cells, benign cells, stromal cells, vascular cells, etc. to interact with each others. In addition, there is also a network of interactions between cytokines and growth factors in the tumor microenvironment. As a result, CAR-T therapy is usually not effective when used in the treatment of solid tumors.

SUMMARY OF THE INVENTION

The purpose of the present invention is to provide a therapy for tumor to improve the application effect of immune cell therapy, especially CAR-T cell therapy, in solid tumors.

In the first aspect of the present invention, provided is a method for treating tumors, comprising administering an immune effector cell and Gemcitabine to an individual suffering from the tumor, wherein the immune effector cell expresses a receptor recognizing a tumor antigen.

In the second aspect of the present invention, also provided is a method for reducing the growth, survival or viability or all the above of a cancer cell, comprising administering an immune effector cell and Gemcitabine to an individual suffering from the tumor, wherein the immune effector cell expresses a receptor recognizing a tumor antigen.

In a preferred embodiment, the immune effector cell and Gemcitabine are administered in no particular order; Gemcitabine can be administered first and then the immune effector cell; they can also be administered at the same time; the immune effector cell can also be administered first and then Gemcitabine. That is, the method of administering the immune effector cell and Gemcitabine to an individual suffering from the tumor is selected from any one of the following: (1) firstly administering Gemcitabine and then the immune effector cell, (2) simultaneously administering the immune effector cell and Gemcitabine, and (3) firstly administering the immune effector cell and then Gemcitabine.

In another preferred embodiment, the above-mentioned receptor is selected from: Chimeric Antigen Receptor (CAR), T cell receptor (TCR), T cell fusion protein (TFP), T cell antigen coupler (TAC), or a combination thereof.

In another preferred embodiment, the tumor antigen is a solid tumor antigen.

In another preferred embodiment, the tumor antigen is selected from the group consisting of: the epidermal growth factor receptor family members and their mutants (i.e., EGFR, EGFR2, ERBB3, ERBB4, EGFRVIII), Claudin 18.2, Claudin 18.1, Claudin 6, glypican-3 (GPC3) and vascular endothelial growth factor receptor.

In another preferred embodiment, the tumor antigen is selected from the group consisting of: thyroid-stimulating hormone receptor (TSHR); CD171; CS-1; C-type lectin-like molecule-1; ganglioside GD3; Tn antigen; CD19; CD20; CD 22; CD 30; CD 70; CD 123; CD 138; CD33; CD44; CD44v7/8; CD38; CD44v6; B7H3 (CD276), B7H6; KIT (CD117); interleukin 13 receptor subunit a (IL-13Rα); interleukin 11 receptor α (IL-11Rα); prostate stem cell antigen (PSCA); prostate specific membrane antigen (PSMA); carcinoembryonic antigen (CEA); NY-ESO-1; HIV-1 Gag; MART-1; gp 100; tyrosinase; mesothelin; EpCAM; protease serine 21 (PRSS21); vascular endothelial growth factor receptor; Lewis (Y) antigen; CD24; platelet-derived growth factor receptor β (PDGFR-β); stage-specific embryonic antigen-4 (SSEA-4); cell surface-associated mucin 1 (MUC1), MUC6; epidermal growth factor receptor family and its mutants (EGFR, EGFR2, ERBB3, ERBB4, EGFRvIII); nerve cell adhesion molecule (NCAM); carbonic anhydrase IX (CAIX); LMP2; ephrin A receptor 2 (EphA2); fucosyl GM1; sialyl Lewis adhesion molecule (sLe); ganglioside GM3(aNeu5Ac(2-3)bDGalp(1-4)bDGlcp(1-1)Cer; TGS5; high molecular weight melanoma-associated antigen (HMWMAA); o-acetyl GD2 ganglioside (OAcGD2); folic acid receptor; tumor vascular endothelial marker 1 (TEM1/CD248); tumor vascular endothelial marker 7 related (TEM7R); Claudin 6, Claudin 18.2, Claudin 18.1; ASGPR1; CDH16; 5T4; 8H9; αvβ6 integrin; B cells mature antigen (BCMA); CA9; kappa light chain; CSPG4; EGP2, EGP40; FAP; FAR; FBP; embryonic AchR; HLA-A1, HLA-A2; MAGEAI, MAGE3; KDR; MCSP; NKG2D ligand; PSC1; ROR1; Sp17; SURVIVIN; TAG72; TEM1; fibronectin; tenascin; carcinoembryonic variant of tumor necrosis zone; G protein-coupled receptor C group 5-member D (GPRC5D); X chromosome open reading frame 61 (CXORF61); CD97; CD179a; anaplastic lymphoma kinase (ALK); polysialic acid; placenta specific 1 (PLAC1); hexose part of globoH glycoceramide (GloboH); breast differentiation antigen (NY-BR-1); uroplakin 2 (UPK2); hepatitis A virus cell receptor 1 (HAVCR1); adrenergic receptor β3 (ADRB3); pannexin 3 (PANX3); G protein-coupled receptor 20 (GPR20); lymphocyte antigen 6 complex locus K9 (LY6K); olfactory receptor 51E2 (OR51E2); TCRY alternating reading frame protein (TARP); Wilms tumor protein (WT1); ETS translocation variant gene 6 (ETV6-AML); sperm protein 17 (SPA17); X antigen family member 1A (XAGE1); angiopoietin-binding cell surface receptor 2 (Tie2); melanoma cancer testis antigen-1 (MAD-CT-1); melanoma cancer testis antigen-2 (MAD-CT-2); Fos-related antigen 1; p53 mutant; human telomerase reverse transcriptase (hTERT); sarcoma translocation breakpoint; melanoma inhibitor of apoptosis (ML-IAP); ERG (transmembrane protease serine 2 (TMPRSS2) ETS fusion gene); N-acetylglucosaminyl transferase V (NA17); pairing box protein Pax-3 (PAX3); androgen receptor; Cyclin B1; V-myc avian myelocytomatosis virus oncogene neuroblastoma derived homolog (MYCN); Ras homolog family member C (RhoC); cytochrome P450 1B1 (CYP1B1); CCCTC binding factor (zinc finger protein)-like (BORIS); squamous cell carcinoma antigen recognized by T-cells 3 (SART3); pairing box protein Pax-5 (PAX5); proacrosin binding protein sp32 (OYTES1); lymphocyte-specific protein tyrosine kinase (LCK); A kinase anchoring protein 4 (AKAP-4); synovial sarcoma, X breakpoint 2 (SSX2); CD79a; CD79b; CD72; leukocyte-associated immunoglobulin-like receptor 1 (LAIR1); Fc fragment of IgA receptor (FCAR); leukocyte immunoglobulin-like receptor subfamily member 2 (LILRA2); CD300 molecular-like family member f (CD300LF); C type lectin domain family 12 member A (CLEC12A); bone marrow stromal cell antigen 2 (BST2); EGF-like module-containing mucin-like hormone receptor-like 2 (EMR2); lymphocyte antigen 75 (LY75); glypican-3 (GPC3); Fc receptor-like 5 (FCRL5); immunoglobulin lambda-like polypeptide 1 (IGLL1).

In another preferred embodiment, the chimeric antigen receptor comprises:

(i) an antibody recognizing a tumor antigen or a fragment thereof, the transmembrane region of CD28 or CD8, the costimulatory signal domain of CD28, and CD3ζ; or (ii) an antibody recognizing a tumor antigen or a fragment thereof, the transmembrane region of CD28 or CD8, the costimulatory signal domain of CD137, and CD3ζ; or (iii) an antibody recognizing a tumor antigen or a fragment thereof, the transmembrane region of CD28 or CD8, the costimulatory signal domain of CD28, the costimulatory signal domain of CD137, and CD3ζ.

In another preferred embodiment, the amino acid sequence of the antibody recognizing a tumor antigen has at least 90% identity with an amino acid sequence shown in any one of SEQ ID NO: 4 and SEQ ID NOs: 14-22; the amino acid sequence of the antibody that recognizes a tumor antigen is an amino acid sequence shown in any one of SEQ ID NO: 4 and SEQ ID NOs: 14-22.

In another preferred embodiment, the amino acid sequence of the chimeric antigen receptor has at least 90% identity with an amino acid sequence shown in any one of SEQ ID NOs: 23-44; preferably the amino acid sequence of the chimeric antigen receptor is an amino acid sequence shown in any one of SEQ ID NOs: 23-44.

In another preferred embodiment, the tumors comprises: breast cancer, colon cancer, rectal cancer, renal cell carcinoma, liver cancer, lung cancer, small intestine cancer, esophageal cancer, melanoma, bone cancer, pancreatic cancer, skin cancer, head and neck cancer, uterine cancer, ovarian cancer, rectal cancer, gastric cancer, testicular cancer, uterine cancer, fallopian tube cancer, endometrial cancer, cervical cancer, vaginal cancer, thyroid cancer, parathyroid cancer, adrenal cancer, soft tissue sarcoma, urethral cancer, penile cancer, bladder cancer, ureteral cancer, renal pelvis cancer, spinal tumor, glioma, pituitary adenoma, Kaposi's sarcoma, a combination of any of the above cancers and metastatic lesions of the above cancers.

In another preferred embodiment, the tumor comprises: breast cancer, blood cancer, colon cancer, rectal cancer, renal cell carcinoma, liver cancer, non-small cell carcinoma of the lung, small intestine cancer, esophageal cancer, melanoma, bone cancer, pancreatic cancer, skin cancer, head and neck cancer, skin or intraocular malignant melanoma, uterine cancer, ovarian cancer, rectal cancer, anal cancer, gastric cancer, testicular cancer, uterine cancer, fallopian tube cancer, endometrial cancer, cervical cancer, vaginal cancer, vulva cancer, Hodgkin's disease, non-Hodgkin's lymphoma, endocrine system cancer, thyroid cancer, parathyroid cancer, adrenal cancer, soft tissue sarcoma, urethral cancer, penile cancer, childhood solid tumor, bladder cancer, renal or ureteral cancer, renal pelvis cancer, central nervous system (CNS) tumor, primary CNS lymphoma, tumor angiogenesis, spinal tumor, brainstem neurospongioma, pituitary adenoma, Kaposi's sarcoma, epidermoid carcinoma, squamous cell carcinoma, T-cell lymphoma, environmentally-induced cancer, a combination of any of the above cancers and metastatic lesions of the above cancers.

In another preferred embodiment, the immune effector cell comprises: T cell, B cell, natural killer (NK) cell, natural killer T (NKT) cell, mast cell, bone marrow-derived phagocytic cell, or a combination thereof; preferably the immune effector cell is selected from autologous T cell, allogeneic T cell, or allogeneic NK cell; more preferably the T cell is an autologous T cell.

In another preferred embodiment, the Gemcitabine is administered by oral administration, intraperitoneal administration and/or injection.

In another preferred embodiment, lymphocyte clearance is not performed on the individual.

In the third aspect of the present invention, provided is use of an immune effector cell expressing a receptor recognizing a tumor antigen in the preparation of a medicament, wherein, the medicament comprises the cell and Gemcitabine, and is used for treating a tumor or reducing the growth, survival or viability of the tumor cells in a human patient, wherein the cell and Gemcitabine are formulated to provide a greater therapeutic effect than the sum of the effects of each of the cell and Gemcitabine when used alone.

In the fourth aspect of the present invention, provided is the use of an immune effector cell expressing a receptor recognizing a tumor antigen and Gemcitabine in the preparation of a medicament, wherein, the medicament is used for treating a tumor or reducing the growth, survival or viability of the tumor cells in a human patient, wherein the cell and Gemcitabine are formulated to provide a greater therapeutic effect than the sum of the effects of each of the cell and Gemcitabine when used alone.

In a preferred embodiment, the immune effector cell is a CAR T cell, preferably, the CAR T cell recognizes the epidermal growth factor receptor family members and their mutants (EGFR, EGFR2, ERBB3, ERBB4, EGFRvIII), Claudin18.2, Claudin18.1, Claudin 6, glypican-3 (GPC3), BCMA and/or vascular endothelial growth factor receptor.

In the fifth aspect of the present invention, provided is a kit for treating tumors, the kit comprises:

1) an immune effector cell expressing a receptor recognizing a tumor antigen;
2) Gemcitabine;
3) a container used for containing the substances described in the above 1) and 2); and
4) administration instructions for using the kit to treat a tumor;

wherein, the cell and Gemcitabine are formulated to provide a greater therapeutic effect than the sum of the effects of each of the cell and Gemcitabine when used alone; preferably, the immune effector cell is a CAR T cell, and more preferably, the CAR T cell recognizes the epidermal growth factor receptor family members and their mutants (EGFR, EGFR2, ERBB3, ERBB4, EGFRVIII), Claudin18.2, Claudin18.1, Claudin 6, glypican-3 (GPC3), BCMA and/or vascular endothelial growth factor receptor.

It should be understood that within the scope of the present invention, the above-mentioned technical features of the present invention and the technical features specifically described in the following (such as the examples) can be combined with each other to form a new or preferred technical solution. Due to space limitations, they are not repeated here one by one.

The beneficial effects of the present invention:

1. The combination of Gemcitabine and the immune effector cells provided by the present invention can significantly improve the ability to kill tumor cells.
2. Adopting the treatment plan of the present invention can resist the immunosuppression in the cancer microenvironment, thereby significantly enhancing the effect on solid tumors, and also having better effects on refractory and progressive cancers.

DETAIL DESCRIPTION OF THE INVENTION

Figure 1:
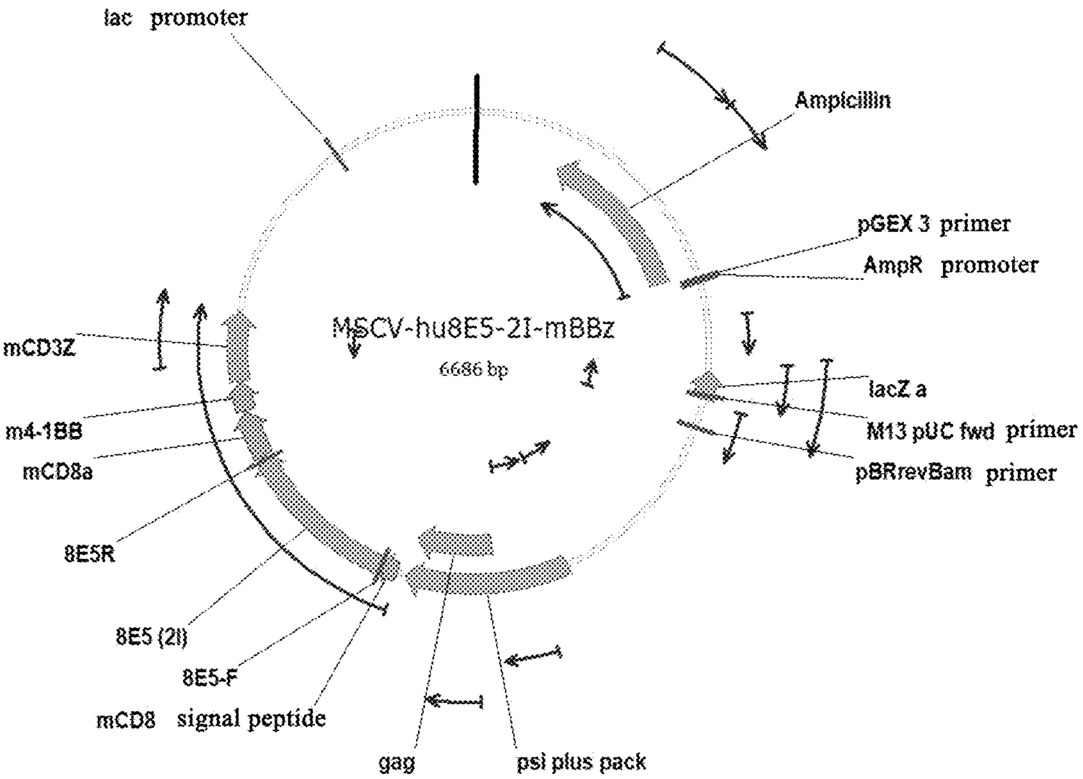
FIG. 1 is a plasmid map of the recombinant vector MSCV-8E5-2I-mBBZ.

The present invention relates to the combined application of immune effector cells and Gemcitabine in the treatment of tumors. It should be understood that the present invention is not limited to the methods and experimental conditions described. Unless specifically defined herein, all technical and scientific terms used have the same meaning as commonly understood by those skilled in the fields of gene therapy, biochemistry, genetics, molecular biology, and medicinal chemistry.

Methods and materials similar or equivalent to those described herein can be used in the practice or testing of the present invention. All publications, patent applications, patents and other references mentioned in this article are incorporated herein in their entirety by reference. In case of conflict, the present specification, including definitions, will control. In addition, unless otherwise stated, the materials, methods, and examples are merely illustrative and not restrictive.

Unless otherwise specified, the practice of the present invention will use traditional techniques of cell biology, cell culture, molecular biology, transgenic biology, microbiology, recombinant DNA and immunology, all of which fall within the technical scope of the art. These techniques are fully explained in the literature. See, for example, Current Protocols in Molecular Biology (FrederickM. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gaited., 1984); Mullis et al. U.S. Pat. No. 4,683,195; Nucleic Acid Hybridization (B. D. Harries & S. J. Higginseds. 1984); Transcription And Translation (B. D. Hames & S. J. Higginseds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), especially Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987,Cold Spring Harbor Laboratory); Immunochemical Methods In Cell And Molecular Biology (Mayer and Walker, eds., Academic Press, London, 1987); Hand book Of Experimental Immunology, vols. I-IV (D. M. Weir and C. C. Blackwell, eds., 1986); and Manipulating the Mouse Embryo (Cold Spring Harbor Laboratory Press, Cold Spring Harbor, N.Y., 1986).

The present invention is at least partly derived from the recognition that one or more cycles and/or doses of a combination treatment regimen of Gemcitabine and immune effector cells administered continuously, in any order or substantially simultaneously, in the treatment of some subjects with cancer can be more effective in increasing, enhancing or prolonging the activity and/or number of immune cells, so as to achieve anti-tumor effects.

The term "Gemcitabine", the chemical name is 2'-deoxy-2', 2'-difluorocytidine hydrochloride; the molecular formula is $C_9H_{11}F_2N_3O_4 \cdot HCl$, and the molecular weight is 299.66. Gemcitabine is a pyrimidine anti-metabolic tumor drug, which can interfere with the synthesis and repair of tumor cell DNA by inhibiting ribonucleotide reductase and cell replication, and is effective for a variety of solid tumors. In specific examples, the combination of Gemcitabine and tumor antigen-targeted immune cell therapy can significantly improve the anti-tumor effect, and even achieve the therapeutic effect of complete remission.

The applicant also found that the present invention can not only improve the anti-cancer effect of refractory cancers, but also require no lymphocyte clearance when using CAR-T cells, thereby greatly reducing the low anti-cancer treatment effect caused by lymphocyte clearance and reducing the toxic side effects caused by damage to normal tissues, especially severe suppression of bone marrow.

In certain embodiments, the dose of Gemcitabine per intravenous infusion for individuals with tumors is about 1250 mg/m$^2$, 1250, 1150, 1100, 1050, 1000, 950, 900, 850, 800, 750, 700, 650, 600, 550, 500, 450, 400, 350, 300, 250, 200, 150, 100, 50, 40, 30, 20, 10, 5, 4, 3, 2 or 1 mg/m$^2$. In certain embodiments, individuals with tumors receive an intravenous infusion of Gemcitabine about once every 6 weeks, 5 weeks, 4 weeks, 3 weeks, 2 weeks, or 1 week.

In the present invention, immune effector cells and Gemcitabine are administrated in no particular order; Gemcitabine can be administrated first and then immune effector cells; Gemcitabine and immune effector cells can also be administrated at the same time; immune effector cells can also be administrated first and then Gemcitabine. In certain embodiments, immune effector cell therapy is 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month, or any combination thereof before Gemcitabine administration. In certain embodiments, immune effector cell therapy is 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month or any combination thereof after Gemcitabine administration.

The term "immune effector cell" refers to a cell that exerts an effect or a function during an immune response. For example, it includes immune cells that secrete cytokines and/or chemokines, kill microorganisms, secrete antibodies, and recognize or eliminate tumor cells. In some embodiments, immune effector cells include T cells (cytotoxic T cells, helper T cells, tumor-infiltrating T cells), B cells, natural killer cells, neutrophils, macrophages (or bone marrow-derived phagocytes) and dendritic cells. Preferably, the T cells include autologous T cells, xenogeneic T cells, and allogeneic T cells, and the natural killer cells are allogeneic NK cells.

As used herein, the term "immunological effect function or immunological effect response" refers to that of immune effector cells, such as functions or responses that enhance or promote immune attack to target cells. For example, immunological effect function or response refers to the properties of T cells or NK cells that promote the killing, or inhibit growth or proliferation of target cells.

The term "immunological effect function" includes any function mediated by the composition of the immune system, which can lead to inhibition of tumor growth and/or inhibition of tumorigenesis, including inhibition of tumor spread and metastasis. Preferably, the immunological effect function kills tumor cells. Preferably, the immunological effect function in the present invention is antibody-mediated, including complement-dependent cytotoxicity (CDC), antibody-dependent cell-mediated cytotoxicity (ADCC), antibody-dependent cell-mediated phagocytosis (ADCP), apoptosis induction in cells carrying tumor-associated antigens (for example, through the binding of antibodies to surface antigens), inhibition of CD40L-mediated signal transduction (for example, through the binding of antibodies to CD40 receptors or CD40 ligands (CD40L)), and/or inhibition of the proliferation of cells carrying tumor-associated antigens, preferably ADCC and/or CDC. Therefore, antibodies capable of mediating one or more immunological effect functions are preferably able to mediate the killing of tumor cells by inducing CDC-mediated lysis, ADCC-mediated lysis, apoptosis, homophilic binding and/or phagocytosis (preferably by inducing CDC-mediated lysis and/or ADCC-mediated lysis). Antibodies can also act simply by binding to tumor-associated antigens on the surface of cancer cells. For example, antibodies can block the function of tumor-associated antigens or induce apoptosis by binding to tumor-associated antigens on the surface of tumor cells.

The terms "therapeutically effective amount", "therapeutically effective", and "effective amount" are used interchangeably herein and refer to the amount of a compound, preparation, substance, or composition that is effective to achieve a specific biological result, such as but is not limited to an amount or dose sufficient to promote a T cell response. When indicating "immunologically effective amount", "anti-tumor effective amount", "effective amount for tumor inhibition" or "therapeutically effective amount", the precise administration amount of immune effector cells or therapeutic agents of the present invention can be determined by the physician in consideration of the individual's age, weight, tumor size, degree of infection or metastasis, and the condition of the patient (subject). An effective amount of immune effector cells refers to but is not limited to the amount of immune effector cells that are able to increase, enhance or prolong the anti-tumor activity of immune effector cells; increase the number of anti-tumor immune effector cells or activated immune effector cells; promote the secretion of IFN-γ and TNFα; and lead to tumor regression, tumor shrinkage, and tumor necrosis.

The term "no lymphocyte clearance" or "without performing lymphocyte clearance" means that the lymphocytes in the subject are not cleared, including but not limited to: without administrating lymphodepleting agent, whole body radiation therapy or a combination thereof, or other means causing lymphocyte clearance; however, after administering lymphodepleting agent, whole body radiation therapy or a combination thereof, or other means leading to lymphocyte clearance, when the lymphocyte clearance rate in the subject is less than 60%, it will fall into the scope of "no lymphocyte clearance" in this application.

The terms "peptide", "polypeptide" and "protein" are used interchangeably and refer to a compound composed of amino acid residues covalently linked by peptide bonds. The protein or peptide must contain at least two amino acids, and there is no limit to the maximum number of amino acids included in the sequence of the protein or peptide. Polypeptides include any peptide or protein containing two or more amino acids joined to each other by peptide bonds. The "chimeric receptor" as used herein refers to a fusion molecule formed by linking DNA fragments or protein corresponding cDNAs from different sources by gene recombination technology, including extracellular domain, transmembrane domain and intracellular domain. Chimeric receptors include but are not limited to: chimeric antigen receptor (CAR), modified T cell (antigen) receptor (TCR), T cell fusion protein (TFP), and T cell antigen coupler (TAC).

As used herein, "chimeric antigen receptor" or "CAR" refers to a set of polypeptides, when they are in an immune effector cell, said cell is provided with specificity against a target cell (usually a cancer cell) and will generate intracellular signal. CAR usually comprises at least one extracellular antigen binding domain, transmembrane domain and cytoplasmic signaling domain (also referred to herein as "intracellular signaling domain"), and it comprises the functional signaling domain of stimulatory molecules and/or costimulatory molecules derived from the following definitions. In certain aspects, groups of polypeptides are adjacent to each other. The group of polypeptides comprises a dimerization switch that may couple polypeptides to each other in the presence of a dimerization molecule, for example, it may couple an antigen binding domain to an intracellular signaling domain. In one aspect, the stimulatory molecule is the & chain binding to the T cell receptor complex. In one aspect, the cytoplasmic signaling domain further comprises one or more functional signaling domains derived from at least one costimulatory molecule as defined below. In one aspect, the costimulatory molecule is selected from the costimulatory molecules described herein, such as 4-1BB (i.e., CD137), CD27, and/or CD28. In one aspect, the CAR comprises a chimeric fusion protein, which comprises an extracellular antigen binding domain, a transmembrane domain, and an intracellular signaling domain comprising a functional signaling domain derived from a stimulatory molecule. In one aspect, the CAR comprises a chimeric fusion protein, which comprises an extracellular antigen binding domain, a transmembrane domain, and intracellular signaling domains of a functional signaling domain derived from a costimulatory molecule and a functional signaling domain derived from a stimulatory molecule. In one aspect, the CAR comprises a chimeric fusion protein, which comprises an extracellular antigen binding domain, a transmembrane domain, and two functional signaling domains derived from one or more costimulatory molecules.

In one aspect, the present invention contemplates modification of the amino acid sequence of the starting antibody or fragment (e.g., scFv) that produces a functionally equivalent molecule. For example, the VH or VL of the antigen-binding domain of the cancer-associated antigen described herein, such as the scFv contained in the CAR, can be modified to retain at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity with the initial VH or VL framework of the antigen-binding domain of the cancer-associated antigen described herein. The present invention contemplates the modification of the entire CAR construct, such as the modification of one or more amino acid sequences of multiple domains of the CAR construct, to produce a functionally equivalent molecule. The CAR construct can be modified to retain at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity with the starting CAR construct.

In a specific embodiment, the amino acid sequence of the antibody recognizing tumor antigen herein has at least 90% identity with the amino acid sequence shown in SEQ ID NO: 4, or shown in SEQ ID NO: 14, or shown in SEQ ID NO: 15, or shown in SEQ ID NO: ID NO: 16, or shown in SEQ ID NO: 17, or shown in SEQ ID NO: 18, or shown in SEQ ID NO: 19, or shown in SEQ ID NO: 20, or shown in SEQ ID NO: 21, or shown in SEQ ID NO: 22; preferably the amino acid sequence shown in SEQ ID NO: 4, or shown in SEQ ID NO: 14, or shown in SEQ ID NO: 15, or shown in SEQ ID NO: 16, or shown in SEQ ID NO: 17, or shown in SEQ ID NO: 18, or shown in SEQ ID NO: 19, or shown in ID NO: 20, or shown in SEQ ID NO: 21, or shown in SEQ ID NO: 22.

As used herein, "transmembrane domain" refers to a region in a protein sequence that spans the cell membrane, and may comprise one or more additional amino acids adjacent to the transmembrane region, for example, one or more amino acids associated with the extracellular region of the protein from which the transmembrane domain is derived (for example, 1, 2, 3, 4, 5, 6, 7, 8, 9, 10 up to 15 amino acids in the extracellular region) and/or one or more other amino acids associated with the extracellular region of the protein from which the transmembrane domain is derived (e.g., 1, 2, 3, 4, 5, 6, 7, 8, 9, 10 up to 15 amino acids in the intracellular region). In one aspect, the transmembrane domain is a domain related to one of the other domains of the chimeric receptor, for example, in one embodiment, the transmembrane domain may be derived from the same protein from which a signaling domain, a costimulatory domain or a hinge domain is derived. In certain cases, a transmembrane domain may be selected or modified by amino acid substitution to prevent such a domain from binding to a transmembrane domain of the same or different surface membrane protein, for example, to minimize the interaction with other member of the receptor complex. In one aspect, the transmembrane domain is capable of homodimerization with another chimeric receptor on the surface of the cell expressing the chimeric receptor. The transmembrane domain may be derived from natural or recombinant sources. When the source is natural, the domain may be derived from any membrane-bound protein or transmembrane protein. In one aspect, the transmembrane domain is capable of transmitting signals to the intracellular domain whenever the chimeric receptor binds to the target. The transmembrane domains specifically used in this application may comprise at least the following transmembrane domains: for example, α, β or ζ chains of a T-cell receptor, CD28, CD27, CD38, CD45, CD4, CD5, CD8, CD9, CD16, CD22, CD33, CD37, CD64, CD80, CD86, CD134, CD137, CD154. In certain embodiments, the transmembrane domains may comprise at least the following transmembrane regions: for example, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2Rβ, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In certain cases, the transmembrane domain may be connected to the extracellular region of the CAR (for example, the antigen binding domain of the CAR) via a hinge (for example, a hinge from a human protein). For example, in one embodiment, the hinge may be a human Ig (immunoglobulin) hinge (e.g., IgG4 hinge, IgD hinge), GS linker (e.g., GS linker described herein), KIR2DS2 hinge, or CD8a hinge. In one aspect, the transmembrane domain can be recombinant, in which case it will mainly contain hydrophobic residues such as leucine and valine. In one aspect, a triplet of phenylalanine, tryptophan and valine can be found at each end of the recombinant transmembrane domain. Optionally, a short oligopeptide or polypeptide linker with 2-10 amino acids in length may form a bond between the transmembrane domain and the cytoplasmic region of the CAR. The glycine-serine dimer provides a particularly suitable linker.

As used herein, "intracellular domain" or "cytoplasmic domain" includes intracellular signaling domain. The intracellular signaling domain is generally responsible for the activation of at least one of the normal immunological effect functions of immune cells into which a chimeric receptor has been introduced. The term "effector function" refers to a specialized function of a cell. The immunological effect function of a T immune cell may be, for example, cytolytic activity or auxiliary activity, including secretion of cytokines. Therefore, the term "intracellular signaling domain" refers to a part of a protein that transduces an immune effector function signal and guides a cell to perform a specific function. Although the entire intracellular signaling domain may usually be used, in many cases it is not necessary to use the entire chain. In the case of using a truncated part of the intracellular signaling domain, such a truncated part, which is able to transduce the immune effector function signal, may be used instead of the complete chain. Therefore, the term intracellular signaling domain is meant to include a truncated part of the intracellular signaling domain sufficient to transduce an immune effector function signal.

It is well known that the signal generated by TCR alone is not sufficient to fully activate T cells, and secondary and/or costimulatory signals are also required. Therefore, T cell activation can be said to be mediated by two different kinds of cytoplasmic signaling sequences: those that trigger antigen-dependent primary activation through TCR (primary intracellular signaling domains) and those that are antigen-independent, and those that act in an antigen-independent manner to provide secondary or costimulatory signals (secondary cytoplasmic domains, such as costimulatory domains).

The term "stimulatory molecule" refers to a molecule expressed by an immune cell (for example, T cell, NK cell, B cell) for providing a cytoplasmic signaling sequence that modulates activation of the immune cell in at least some aspects of the signaling pathways for immune cells in a stimulating manner. In one aspect, the signal is a primary signal initiated by for example the binding of the TCR/CD3 complex and the MHC-antigen peptide complex, and it leads to mediation of T cell responses, including but not limited to: proliferation, activation, differentiation, and the like. The primary cytoplasmic signaling sequence (also referred to as "primary signaling domain") acting in a stimulating manner may contain a signaling motif called an immune-receptor tyrosine-based activation motif or ITAM. Examples of ITAM-containing cytoplasmic signaling sequences specifically used in this application include, but are not limited to, those derived from: CD3ζ, common FcRγ (FCER1G), FcγRIIa, FcRβ (FcEpsilon R1b), CD3γ, CD3δ, CD3ε, CD79a, CD79b, DAP10 and DAP12. The intracellular signaling domain in any one of the CARs of this application comprises intracellular signaling sequences, such as the primary signaling sequence of CD3-ζ. In the specific CAR of the application, the primary signaling sequence of CD3-ζ is the equivalent residues from human or non-human species such as mouse, rodent, monkey, ape and the like.

The term "costimulatory molecule" refers to a homologous binding partner on T cells, which specifically binds to a costimulatory ligand, thereby mediating the costimulatory response of T cells, such as but not limited to proliferation. Co-stimulatory molecules are cell surface molecules excluding antigen receptors or the ligands thereof, which promote effective immune responses. The co-stimulatory molecules include but are not limited to: MHC class I molecules, BTLA and Toll ligand receptors, as well as OX40, CD27, CD28, CDS, ICAM-1, LFA-1 (CD11a/CD18), ICOS (CD278) and 4-1BB (CD137). Further examples of such costimulatory molecules include: CDS, ICAM-1, GITR, BAFFR, HVEM (LIGHTR), SLAMF7, NKp80 (KLRF1), NKp44, NKp30, NKp46, CD160, CD19, CD4, CD8a, CD8B, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1 CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and ligands specifically binding to CD83.

The costimulatory intracellular signaling domain may be the intracellular part of a costimulatory molecule. Costimulatory molecules may be represented by the following protein families: TNF receptor protein, immunoglobulin-like protein, cytokine receptor, integrin, Signaling lymphocytic activation molecule (SLAM protein), and NK cell receptor. Examples of such molecules include: CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and ligands specifically binding to CD83, etc.

The intracellular signaling domain may include all the intracellular part or all the natural intracellular signaling domain of the molecule, or a functional fragment or derivative thereof.

The term "4-1BB" refers to a member of the TNFR superfamily with the amino acid sequence provided in GenBank Accession No. AAA62478.2, or equivalent residues from non-human species such as mouse, rodent, monkey, ape and the like; and "4-1BB costimulatory domain" is defined as the amino acid residues 214-255 of GenBank Accession No. AAA62478.2, or equivalent residues from non-human species such as mouse, rodent, monkey, ape and the like. In one aspect, the "4-1BB costimulatory domain" is an equivalent residue from human or from non-human species such as mouse, rodent, monkey, ape and the like.

The chimeric antigen receptor herein has: (i) an antibody recognizing a tumor antigen or a fragment thereof, the transmembrane region of CD28 or CD8, the costimulatory signal domain of CD28, and CD32; or (ii) an antibody recognizing a tumor antigen or a fragment thereof, the transmembrane region of CD28 or CD8, the costimulatory signaling domain of CD137, and CD32; or (iii) an antibody recognizing a tumor antigen or a fragment thereof, the transmembrane region of CD28 or CD8, the costimulatory signaling domain of CD28, the costimulatory signaling domain of CD137, and CD3ζ.

The amino acid sequence of the chimeric antigen receptor herein has at least 90% identity with the amino acid sequence shown in SEQ ID NO: 23, 24, 25, 26, 27, 28, 29, 30, 31, 32, 33, 34, 35, 36, 37, 38, 39, 40, 41, 42, 43 or 44; preferably the amino acid sequence of the chimeric antigen receptor is the amino acid sequence shown in SEQ ID NO: 23, 24, 25, 26, 27, 28, 29, 30, 31, 32, 33, 34, 35, 36, 37, 38, 39, 40, 41, 42, 43 or 44.

The term "antibody" refers to a protein or polypeptide sequence derived from an immunoglobulin molecule specifically binding to an antigen. An antibody may be multiclonal or monoclonal, multi-chain or single-chain, or a whole immunoglobulin, and may be derived from a natural source or recombinant source. The antibody may be the tetramer of an immunoglobulin molecule.

The term "antibody fragment" refers to at least a portion of an antibody that retains the ability to specifically interact with an epitope of an antigen (e.g., through binding, steric hindrance, stabilization/destabilization, spatial distribution). Examples of antibody fragments include, but are not limited to: Fab, Fab', $F(ab')_2$, Fv fragment, scFv, disulfide-linked Fvs (sdFv), Fd fragment composed of VH and CH1 domains, linear antibody, single domain antibody (such as sdAb), camelid VHH domain, multispecific antibody formed by antibody fragments (e.g., a bivalent fragment comprising two Fab fragments connected by disulfide bonds in the hinge region), and isolated CDRs of an antibody or other epitope binding fragments. The term "scFv" refers to a fusion protein comprising at least one antibody fragment including a variable region of a light chain and at least one antibody fragment including a variable region of a heavy chain, wherein the light chain and heavy chain variable regions are contiguous (for example, via a synthetic linker such as a short flexible polypeptide linker), and may be expressed as a single-chain polypeptide, and wherein the scFv retains the specificity of the intact antibody from which it is derived. Unless specified, as used herein, the scFv may have the VL and VH variable regions in any order (for example, relative to the N-terminus and C-terminus of the polypeptide), and the scFv may comprise VL-linker-VH, or may comprise VH-linker-VL.

The term "antibody heavy chain" refers to the larger of the two polypeptide chains which is present in an antibody molecule in its naturally occurring configuration and usually determines the type of antibody to which it belongs.

The term "antibody light chain" refers to the smaller of the two polypeptide chains which is present in an antibody molecule in its naturally occurring configuration. Kappa (k) and lambda (l) light chains refer to isotypes of the two main antibody light chains.

The term "recombinant antibody" refers to an antibody produced by recombinant DNA technology, such as, for example, an antibody expressed by a phage or yeast expression system. The term should also be interpreted as referring to an antibody that has been produced by synthesizing a DNA molecule encoding the antibody (and wherein the DNA molecule expresses the antibody protein) or the amino acid sequence of the specified antibody, wherein the DNA or amino acid sequence has been obtained by recombinant DNA technology or an amino acid sequence technology available and well-known in the art.

The term "antigen" or "Ag" refers to a molecule that causes an immune response. The immune response may involve the production of antibodies or the activation of cells with specific immunity or both. Those skilled in the art should understand that, any macromolecule including virtually all proteins or peptides may serve as an antigen. In addition, an antigen may be derived from recombinant or genomic DNA. When the term is used herein, those skilled in the art should understand that, any DNA comprising a nucleotide sequence or part of a nucleotide sequence that encodes a protein causing an immune response may encode an "antigen." In addition, those skilled in the art should understand that, an antigen need not to be encoded only by the full-length nucleotide sequence of a gene. This application includes, but is not limited to, utilizing partial nucleotide sequences of more than one gene, and these nucleotide sequences are arranged in different combinations to encode polypeptides that elicit a desired immune response. Those skilled in the art should understand that, an antigen does not need to be encoded by a "gene" at all. An antigen may be produced synthetically, or it may be derived from a biological sample, or it may be a macromolecule other than a polypeptide. Such biological samples may include, but are not limited to: tissue samples, tumor samples, cells or fluids having other biological components.

The term "tumor-associated antigen (TAA)" or "tumor antigen" refers to a protein specifically expressed in a limited number of tissues and/or organs under normal conditions or in a specific stage of development. In some embodiments, the tumor-associated antigen is specifically expressed in gastric tissue under normal conditions, preferably in the pancreas, gastric mucosa, in the reproductive organs (e.g., testis), in trophoblast tissue (e.g., placenta), or in germline cells, and it is expressed or abnormally expressed in one or more tumor tissues or cancer tissues. In some embodiments, the tumor-associated antigen refers to a differentiation antigen, preferably a cell type-specific differentiation antigen, that is, a protein specifically expressed in a cell type at a specific differentiation stage under normal conditions. In some embodiments, tumor-associated antigens are located in tumor cells, but are not expressed or only slightly expressed in normal tissues. In some embodiments, tumor-associated antigens or abnormal expression of tumor-associated antigens can be used to identify tumor cells. In some embodiments, the tumor-associated antigen expressed by tumor cells in an individual (for example, a tumor patient) is the individual's autologous protein. In some embodiments, the tumor-associated antigen is specifically expressed under normal conditions in tissues or organs that are not lethal when an individual is injured by the immune system; or is specifically expressed in organs or structures that are inaccessible or difficult to access by the body's immune system. In some embodiments, the amino acid sequence of the tumor-associated antigen expressed in normal tissues is the same as the amino acid sequence of the tumor-associated antigen expressed in tumor tissues.

The tumor antigens of the present invention include but are not limited to: thyroid stimulating hormone receptor (TSHR); CD171; CS-1; C-type lectin-like molecule-1; ganglioside GD3; Tn antigen; CD19; CD20; CD 22; CD 30; CD70; CD123; CD138; CD33; CD44; CD44v7/8; CD38; CD44v6; B7H3 (CD276), B7H6; KIT (CD117); interleukin 13 receptor subunit α (IL-13Rα); interleukin 11 receptor α (IL-11Rα); prostate stem cell antigen (PSCA); prostate specific membrane antigen (PSMA); carcinoembryonic antigen (CEA); NY-ESO-1; HIV-1 Gag; MART-1; gp100; tyrosine enzyme; mesothelin; EpCAM; protease serine 21 (PRSS21); vascular endothelial growth factor receptor, vascular endothelial growth factor receptor 2 (VEGFR2); Lewis (Y) antigen; CD24; platelet derived growth factor receptor β (PDGFR)-β); stage-specific embryonic antigen-4 (SSEA-4); cell surface-associated mucin 1 (MUC1), MUC6; epidermal growth factor receptor family and its mutants (EGFR, EGFR2, ERBB3, ERBB4, EGFRVIII); nerve cell adhesion molecule (NCAM); carbonic anhydrase IX (CAIX); LMP2; ephrin A receptor 2 (EphA2); fucosyl GM1; sialyl Lewis adhesion molecule (sLe); ganglioside GM3; TGS5; high molecular weight melanoma-associated antigen (HMW-MAA); o-acetyl GD2 ganglioside; folate receptor; tumor vascular endothelial marker 1 (TEM1/CD248); tumor vascular endothelial marker 7 related (TEM7R); Claudin6, Claudin 18.2, Claudin 18.1; ASGPR1; CDH16; 5T4; 8H9; αvβ6 integrin; B cell maturation antigen (BCMA); CA9; kappa light chain; CSPG4; EGP2, EGP40; FAP; FAR; FBP; embryonic AchR; HLA-A1, HLA-A2; MAGEA1, MAGE3; KDR; MCSP; NKG2D ligand; PSC1; ROR1; Sp17; SURVIVIN; TAG72; TEM1; fibronectin; tenascin; carcinoembryonic variant of tumor necrosis zone; G protein-coupled receptor C group 5-member D (GPRC5D); X chromosome open reading frame 61 (CXORF61); CD97; CD179a; anaplastic lymphoma kinase (ALK); polysialic acid; placenta specific 1 (PLAC1); the hexose part of globoH glycoceramide (GloboH); breast differentiation antigen (NY-BR-1); uroplakin 2 (UPK2); hepatitis A virus cell receptor 1 (HAVCR1); adrenergic receptor β3 (ADRB3); pannexin 3 (PANX3); G protein coupling Receptor 20 (GPR20); lymphocyte antigen 6 complex locus K9 (LY6K); olfactory receptor 51E2 (OR51E2); TCRY alternating reading frame protein (TARP); Wilms tumor protein (WT1); ETS translocation variant gene 6 (ETV6-AML); sperm protein 17 (SPA17); X antigen family member 1A (XAGE1); angiopoietin-binding cell surface receptor 2 (Tie2); melanoma cancer testis antigen-1 (MAD-CT-1); melanoma cancer testis antigen-2 (MAD-CT-2); Fos-related antigen 1; p53 mutant; human telomerase reverse transcriptase (hTERT); sarcoma translocation breakpoint; melanoma inhibitor of apoptosis protein (ML-IAP); ERG (transmembrane protease serine 2 (TMPRSS2) ETS fusion gene); N-acetylglucosaminyl transferase V (NA17); paired box protein Pax-3 (PAX3); male hormone receptor; Cyclin B1; V-myc avian myelocytomatosis viral oncogene neuroblastoma derived homolog (MYCN); Ras homolog family member C (RhoC); cytochrome P450 1B1 (CYP1B1); CCCTC binding factor (zinc finger protein)-like (BORIS); squamous cell carcinoma antigen 3 recognized by T cells (SART3); paired box protein Pax-5 (PAX5); proacrosin binding protein sp32 (OYTES1); lymphocytes specific protein tyrosine kinase (LCK); A kinase anchoring protein 4 (AKAP-4); synovial sarcoma X breakpoint 2 (SSX2); CD79a; CD79b; CD72; leukocyte-associated immunoglobulin-like receptor 1 (LAIR1); Fc fragment of IgA receptor (FCAR); leukocyte immunoglobulin-like receptor subfamily member 2 (LILRA2); CD300 molecule-like family member f (CD300LF); C-type lectin domain family member A (CLEC12A); bone marrow stromal cell antigen 2 (BST2); EGF-like module-containing mucin-like hormone receptor-like 2 (EMR2); lymphocyte antigen 75 (LY75); glypican-3 (GPC3); Fc receptor-like 5 (FCRL5); immunoglobulin lambda-like polypeptide 1 (IGLL1).

The term "tumor" refers to swelling or a lesion caused by abnormal cell growth (called neoplastic cell or tumor cell). "Tumor cell" refer to a cell that can proliferate rapidly and uncontrollably, and an abnormal cell that continues to grow after the stimulus that caused the proliferation ceases. Tumors appear as partial or complete lack of structural tissue, and lack of functional coordination with normal tissues, usually forming unique tissue masses, which can be benign, pre-malignant or malignant.

The term "cancer" (medical term: malignant tumor) is a type of disease in which a group of cells exhibit uncontrolled growth (division beyond normal limits), invasion (invasion and destruction of adjacent tissues) and sometimes metastasis (through lymph or the blood spreads to other parts of the body). These three malignant characteristics of cancer distinguish them from benign tumors, which are self-limiting and do not invade or metastasize. Most cancers form tumors, but some (such as leukemia) do not.

The terms "cancer" and "tumor" or "cancer disease" and "tumor disease" are interchangeable and refer to diseases in which cells exhibit uncontrolled growth, and/or invasion, and/or metastasis, including leukemia, seminoma, melanoma, teratoma, lymphoma, neuroblastoma, glioma, rectal cancer, endometrial cancer, kidney cancer, adrenal cancer, thyroid cancer, blood cancer, skin cancer, brain cancer, cervical cancer, bowel cancer, liver cancer, colon cancer, stomach cancer, bowel cancer, head and neck cancer, gastrointestinal cancer, lymph node cancer, esophageal cancer, colorectal cancer, pancreatic cancer, ear, nose and throat (ENT) cancer, breast cancer, prostate cancer, uterine cancer, ovarian cancer and lung cancer, and their metastasis. Examples include lung cancer, breast cancer, prostate cancer, colon cancer, renal cell carcinoma, cervical cancer, or metastasis of the above-mentioned various cancers or tumors.

The term "transfected", or "transduced" refers to the process by which exogenous nucleic acid is transferred or introduced into a host cell. A "transfected", or "transduced" cell is a cell being transfected, transformed, or transduced with exogenous nucleic acid. The cells include primary subject cells and their progeny.

The terms "specifically bind" and "specifically recognize" have the same meaning herein, refers to an antibody or ligand that recognizes and binds a protein of a binding partner (such as a tumor antigen) present in a sample, but the antibody or ligand does not substantially recognize or bind to other molecules in the sample.

The term "refractory" refers to a disease, such as a cancer or a tumor, which does not respond to treatment. In an embodiment, a refractory tumor may be resistant to the treatment before or at the beginning of the treatment. In other embodiments, a refractory tumor may become resistant during treatment. Refractory cancers are also called resistant tumors. In this application, refractory tumors include, but are not limited to, tumors that are not sensitive to radiotherapy, relapse after radiotherapy, are not sensitive to chemotherapy, relapse after chemotherapy, are not sensitive to CAR-T treatment, or relapse after the treatment. Refractory or recurrent malignant tumors can use the treatment regimens described herein.

As used herein, "relapsed" refers to the return of the signs and symptoms of a disease (e.g. cancer) or a disease such as cancer during a period of improvement, for example, after a therapy, such as a previous treatment of cancer therapy.

The terms "subject", "individual", "organism" or "patient" are used interchangeably and include vertebrates, preferably mammals. In the present invention, mammals are humans, non-human primates, domestic animals (e.g., dogs, cats, sheep, cattle, goats, pigs, horses, etc.), experimental animals (e.g., mice, rats, rabbits, guinea pigs, etc.) and animals in captivity (e.g., zoo animals). The term "animal" as used herein also includes humans. The terms "subject" and "individual" include patients, i.e., diseased animals, preferably humans, and the disease is preferably the disease described herein.

The term "enhancement" refers to allowing a subject or tumor cell to improve its ability to respond to the treatment disclosed herein. For example, an enhanced response may include 5%, 10%, 15%, 20%, 25%, 30%, 35%, 40%, 45%, 50%, 55%, 60%, 65%, 70%, 75%, 80%, 85%, 90%, 95% or 98% or more enhancement of the responsiveness. As used herein, "enhancement" may also refer to increasing the number of subjects responding to treatment, such as immune effector cell therapy. For example, an enhanced response may refer to the total percentage of subjects responding to treatment, wherein the percentages are 5%, 10%, 15%, 20%, 25%, 30%, 35%, 40%, 45%, 50%, 55%, 60%, 65%, 70%, 75%, 80%, 85%, 90%, 95%, or 98%, or more.

In one aspect, treatment is determined by the following clinical outcomes: increase, enhancement or extension of the anti-tumor activity of T cells; the increase in the number of anti-tumor T cells or activated T cells as compared with the number before treatment, promotion of the secretion of IFN-γ, TNFa, or a combination thereof. In another aspect, the clinical outcome is tumor regression; tumor shrinkage; tumor necrosis; anti-tumor response through the immune system; tumor enlargement, recurrence or spread, or a combination thereof. In an additional aspect, the therapeutic effect is predicted by the presence of T cells, the presence of genetic markers indicative of T cell inflammation, promotion of IFN-γ, TNFa secretion, or a combination thereof.

The immune effector cells as disclosed herein may be administered to an individual by various routes, including, for example, orally or parenterally, such as intravenous, intramuscular, subcutaneous, intraorbital, intrasaccular, intraperitoneal, intrarectal, intracisternal, intratumoral, intranasally, intradermally, or passive or promoted absorption through the skin by respectively using, for example, skin patches or transdermal iontophoresis.

The total amount of agent to be administered in practicing the method according to the present application may be administered to a subject as a single dose as a bolus or by infusion over a relatively short period of time; or may be administered using a graded treatment regimen, wherein multiple doses are administered over an extended period of time. Those skilled in the art will know that, the amount of the composition for treating a pathological condition in a subject depends on many factors, including the age and general health of the subject, as well as the route of administration and the number of treatments to be administered. In consideration of these factors, the technician will adjust the specific dosage as needed. Generally speaking, the phase I and phase II clinical trials are initially used to determine the formulation of the composition and the route and frequency of administration.

Scope: throughout this disclosure, various aspects of this application may be presented in a range format. It should be understood that, the description of range format is only for convenience and brevity, and should not be regarded as an unchangeable limitation on the scope of the application. Therefore, the description of a range should be considered as specifically disclosing all possible subranges and individual values within that range. For example, a description of a range such as 1-6 should be considered to specifically disclose the subranges such as 1-3, 1-4, 1-5, 2-4, 2-6, 3-6, etc., and the individual values within the range, for example, 2, 2.7, 3, 4, 5, 5.3, and 6. As another example, a range such as 95-99% identity includes a range with 95%, 96%, 97%, 98%, or 99% identity, and includes sub-ranges such as 96-99%, 96-98%, 96-97%, 97-99%, 97-98% and 98-99% identity. This applies regardless of the width of the range.

Based on the present disclosure, those skilled in the art should understand that, many changes or modifications may be made in the disclosed specific embodiments and still obtain the same or similar results without departing from the spirit and scope of the present invention. The scope of the present invention is not limited to the specific embodiments described herein (which are only intended to be an illustration of various aspects of the present invention), and the functionally equivalent methods and components are within the scope of the present invention.

This application relates to adoptive cells or immune effector cells to treat solid tumors, including administering multiple or repeated doses of cells, and methods, compositions and products used thereof. Cells generally express chimeric antigen receptors such as chimeric antigen receptors (CARs) or other transgenic receptors such as T cell receptors (TCRs).

Human claudin 18 (Claudin 18, CLD18) molecules (Genbank accession number: splice variant 1 (CLD18A1 or Claudin 18.1): NP_057453, NM016369, and splice variant 2 (CLD18A2 or Claudin 18.2): NM_001002026, NP_001002026) is an internal transmembrane protein with a molecular weight of about 27, 9/27, 72 kD. Murine Claudin 18.2 (NP_001181850.1).

The term "CLD18" refers to claudin 18 and includes any variants of CLD18 (including CLD18A1 and CLD18A2), conformations, isoforms, and interspecies homologs that are naturally expressed by cells or expressed by cells transfected with the CLD18 gene. Claudin 18 is an internal membrane protein located in the tight junction of epithelium and endothelium, tightly connected to a network of interconnected chains of particles in the tissue membrane between adjacent cells. In tight junctions, occludin and claudin are the most important transmembrane protein components. Due to their strong intercellular adhesion properties, they create a primary barrier that prevents and controls the paracellular transport of solutes and restricts the lateral diffusion of membrane lipids and proteins to maintain cell polarity. The proteins that form tight junctions are critically involved in the tissues structure of epithelial tissue. Preferably, "CLD18" refers to human CLD18, especially CLD18A2 (amino acid sequence is shown in SEQ ID NO: 2) and/or CLD18A1 (amino acid sequence is shown in SEQ ID NO: 3), more preferably CLD18A2.

The term "CLD18A1" includes any post-translational modified variants, isoforms and interspecies homologs of human CLD18A1 that are naturally expressed by cells or expressed by cells transfected with the CLD18Al gene.

The term "CLD18A2" includes any post-translational modified variants, isoforms and interspecies homologs of human CLD18A2 that are naturally expressed by cells or expressed by cells transfected with the CLD18A2 gene.

The term "CLD18 variant" shall include (i) CLD18 splice variants, (ii) CLD18 post-translational modification variants, especially including variants with different N glycosylation states, (iii) CLD18 conformational variants, especially including CLD18-conformation-1, CLD18-conformation-2 and CLD18-conformation-3, (iv) free CLD18 and homotypic/heterotypic-associated variants located at tight junctions between cells, (v) CLD18 cancer-related variants and CLD18 non-cancer-related variants.

In some embodiments, the claudin 18A2 is a peptide comprising the amino acid sequence of SEQ ID NO: 2 or a protein/peptide of a variant of the amino acid sequence. The term "variant" refers to mutants, splice variants, conformations, isoforms, allelic variants, species variants and species homologs, especially naturally occurring variants. The terms "CLDN", "CLDN18", "CLDN18A1" and "CLDN18A2" shall encompass any post-translationally modified variants and conformational variants.

CLD18A1 is selectively expressed in the epithelium of normal lung and stomach, while CLD18A2 is only expressed in gastric cells. Moreover, CLD18A2 is limited to differentiated short-lived gastric epithelial cells, but does not exist in the gastric stem cell area.

In some embodiments, the primary tumor refers to gastric cancer, esophageal cancer, pancreatic cancer, lung cancer such as non-small cell lung cancer, ovarian cancer, colon cancer, liver cancer, head and neck cancer, and gallbladder cancer, and the metastasis particularly refers to gastric cancer metastasis such as Krukenberg Tumor, peritoneal metastasis and lymph node metastasis. In some embodiments, the cells expressing CLDN18A2 refer to tumor cells, and are particularly selected from the group consisting of tumorigenic gastric cancer cells, esophageal cancer cells, pancreatic cancer cells, lung cancer cells, ovarian cancer cells, colon cancer cells, liver cancer cells, head and neck cancers cells and gallbladder cancer cells.

In some embodiments, the tumor includes: breast cancer, colon cancer, rectal cancer, renal cell cancer, liver cancer, lung cancer, small intestine cancer, esophageal cancer, melanoma, bone cancer, pancreatic cancer, skin cancer, head and neck cancer, uterine cancer, ovarian cancer, rectal cancer, gastric cancer, testicular cancer, uterine cancer, fallopian tube cancer, endometrial cancer, cervical cancer, vaginal cancer, thyroid cancer, parathyroid cancer, adrenal cancer, soft tissue sarcoma, urethral cancer, penile cancer, bladder cancer, ureteral cancer, renal pelvis cancer, spinal tumors, gliomas, pituitary adenomas, Kaposi's sarcoma, a combination of any of the above cancers and metastatic lesions of the above cancers.

The present invention provides a therapeutic method and composition for treating diseases (such as tumors) with CLD18 expression.

The present invention provides a method for treating tumors in a subject in adoptive cell or immune effector cell therapy for solid tumors, in which the subject expresses genetically engineered (recombined) immune effector cell chimeric receptors. The method generally includes a single course of reinfusion or multiple course of reinfusion of such cells. In some embodiments, it is a dose escalation within a course of treatment, repeated dose infusion within a course of treatment, or a dose decrease within a course of treatment. In some embodiments, the first dose is a lower dose and/or an adjusted or reduced dose and/or the subsequent dose is a consolidated dose and/or an adjusted or reduced dose. Also provided are cells, compositions, and articles that can be used in such methods. In some embodiments, the chimeric receptor is a genetically engineered antigen receptor, such as a functional non-TCR antigen receptor, for example, a chimeric antigen receptor (CAR) and other recombinant antigen receptors, such as transgenic T cell receptors (TCRs). Receptors also include other recombinant chimeric receptors, such as those containing extracellular and intracellular portions that specifically bind to ligands or receptors or other binding partners, such as the intracellular signal transduction portion of the CAR. In some embodiments, the dose includes a lower first dose.

In some embodiments, the method comprises (a) administering a single course of cells expressing chimeric antigen receptors (e.g., CARs) to a subject with a tumor; and (b) administering multiple courses of cells expressing chimeric antigen receptors (e.g., CARs) to the subject. In other embodiments, one or more subsequent doses may be administered.

The present invention will be further explained below in conjunction with specific examples. It should be understood that, these examples are only used to illustrate the present invention and not to limit the scope of the present invention. The following examples without specified experimental methods of specific conditions usually follow conventional conditions such as those described in J. Edited by Sambrook et al., "Molecular Cloning Experiment Guide (Third Edition)" (Science Press, 2002), or those recommended by the manufacturer.

Exemplary antigen receptors of the present application, including CAR, and methods for engineering and introducing receptors into cells, may refer to, those described in, for example, Chinese patent application publication Nos. CN107058354A, CN107460201A, CN105194661A, CN105315375A, CN105713881A, CN106146666A, CN106519037A, CN106554414A, CN105331585A, CN106397593A, CN106467573A, and CN104140974A; and international patent application publications Nos. WO2017186121A1, WO2018006882A1, WO2015172339A8 and WO2018018958A1.

Example 1. Panc02/Luc-GFP-Claudin 18.2, 8E5-2I-mBBZ CAR T Cell Establishment 1. Construction of Panc02/Luc-GFP-Claudin 18.2 Cells The Panc02 pancreatic cancer cell model overexpressing murine Claudin 18.2 (SEQ ID NO: 1) is established using conventional methods of molecular biology (the Panc02 pancreatic cancer cell model is purchased from BeiNa Biotech). Using pWPT as a vector, insert murine Claudin 18.2 (SEQ ID NO: 1) to construct plasmid pWPT-mClaudin 18.2. Then the pancreatic cancer cell Panc02/Luc-GFP-Claudin 18.2 overexpressing murine Claudin 18.2 is established by lentivirus packaging infection method.

2. Construction of T Cells Expressing Chimeric Antigen Receptors (1) Plasmid Construction Using conventional molecular biology methods in the art, the scFv used in this example is a murine claudin 18.2-targeting antibody, and the nucleic acid sequence is shown in SEQ ID NO:5.

Using MSCV-IRES-GFP (purchased from Addgene) as a vector, a retroviral plasmid MSCV-8E5-2I-mBBZ expressing the second-generation chimeric antigen receptor is constructed (as shown in FIG. 1). Wherein, the 8E5-2I-mBBZ sequence is consisted of murine CD8α signal peptide (its amino acid sequence is shown in SEQ ID NO: 6 and its nucleotide sequence is shown in SEQ ID NO: 7), scFv targeting claudin 18.2 (its amino acid sequence is shown in SEQ ID NO: 4 and its nucleotide sequence is shown in SEQ ID NO: 5), the murine CD8 hinge and the transmembrane region (its amino acid sequence is shown in SEQ ID NO: 8 and its nucleotide sequence is shown in SEQ ID NO: 9) and murine 4-1BB intracellular signaling domain (its amino acid sequence is shown in SEQ ID NO: 10 and its nucleotide sequence is shown in SEQ ID NO: 11) and murine CD3 intracellular segment CD3ζ (its amino acid sequence is shown in SEQ ID NO: 12 and its nucleotide sequence is shown in SEQ ID NO: 13).

The MSCV-8E5-2I-mBBZ constructed above is transfected into 293T (from ATCC) to package the retrovirus to obtain the retrovirus. The infection method is a conventional infection method in the preparation process of T cells expressing chimeric antigen receptors in the art.

(2) CAR T cell construction: take the spleen T lymphocytes of C57BL/6 mice (from Shanghai Xipuer-Bikai laboratory Animal Limited Company), add the purified murine CD3+ T lymphocytes to Dynabeads Mouse T-activator CD3/CD28 at a volume ratio of 1:1, wash once with PBS, activate, culture in incubator. The medium is RPMI 1640 complete medium (purchased from invitrogen company). 10% FBS serum is added.

The murine spleen T lymphocytes activated for 24 hours are inoculated into a 12-well plate coated with recombinant human fibrin fragments. Retrovirus is added for infection for 12 hours, and then cultured and amplified to the required number to obtain murine 8E5-2I-mBBZ CAR T cells.

Example 2. In Vivo Experiment to Observe the Inhibitory Effect of the Combination of Gemcitabine and CAR T Cells on Mouse Pancreatic Cancer The pancreases of 6-week-old C57BL/6 mice are inoculated with $2\times10^5$ Panc02/Luc-GFP-Claudin 18.2 cells in situ, and is recorded as Day 0 in the tumor cell inoculation diary.

On the 6th day after tumor inoculation (i.e., Day 6), mouse T cells are taken and constructed according to Example 1 to construct the 8E5-2I-mBBZ CAR T cell line. At the same time, the mice are subjected to in vivo imaging, and the mice are randomly grouped according to the tumor burden of the mice. The main groups are:

Group 1: UTD group, that is, the group administrated only untransfected mouse T cell treatment;

Group 2: CART group, that is, the group administrated only 8E5-2I-mBBZ CAR T cell therapy;

Group 3: Gemcitabine group, that is, the group administrated only Gemcitabine; and Group 4: Gemcitabine+CART group, that is, the group administrated 8E5-2I-mBBZ CAR T cells combined with Gemcitabine treatment.

On the 6th, 7th, and 8th day (i.e., Day 6, 7, and 8), mice in the Gemcitabine group and Gemcitabine+CART group are administrated 30 mg/kg Gemcitabine for treatment, intraperitoneal administration, once a day.

On the 9th day (i.e., Day 9) after tumor inoculation, mice in the CART group and Gemcitabine+CART group are administrated a dose of $3\times10^6$ 8E5-2I-mBBZ CAR-T cells through the tail vein injection, respectively, and the UTD group is administrated $3\times10^6$ untransfected mouse T cells by injection, and then live imaging is performed once a week to observe the therapeutic effect.

Figure 2:
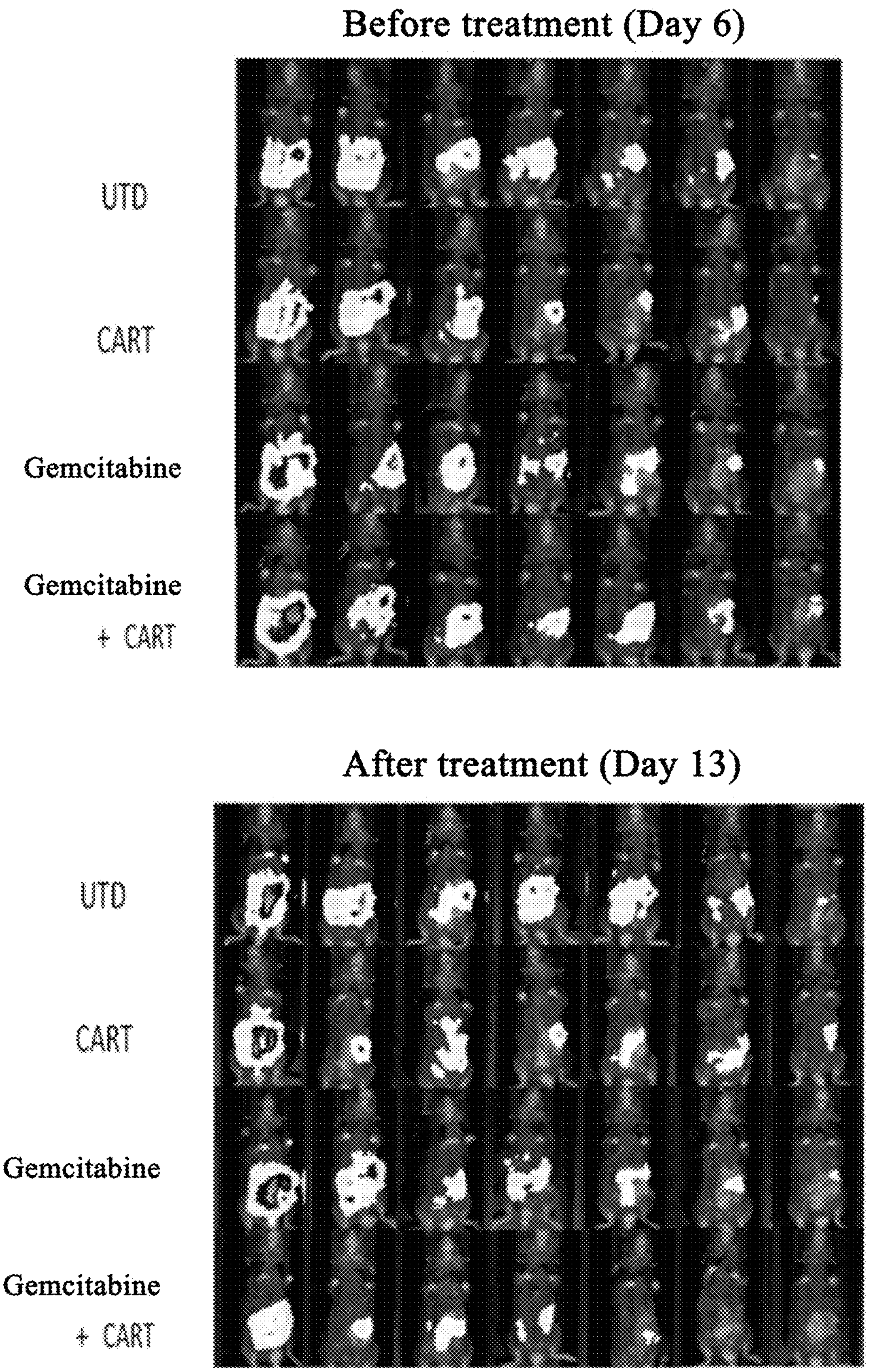
FIG. 2 shows the observed inhibitory effect of the combination of Gemcitabine and CART cells on in situ pancreatic cancer in mice in in vivo experiment.
Figure 2:
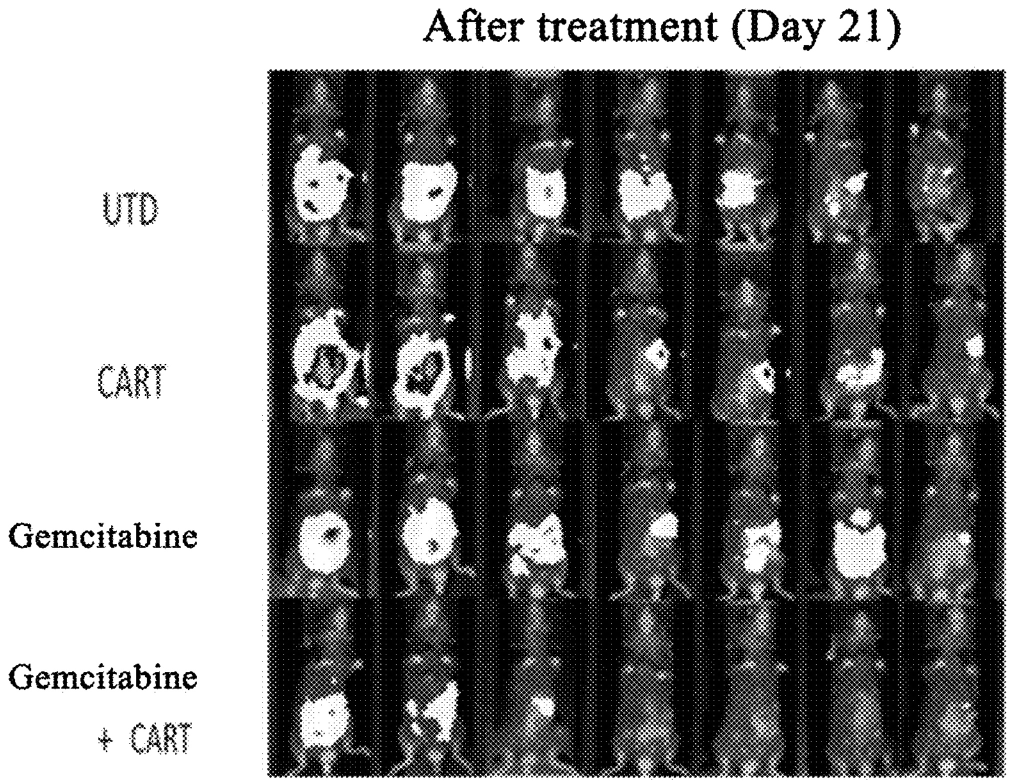
Figure 3:
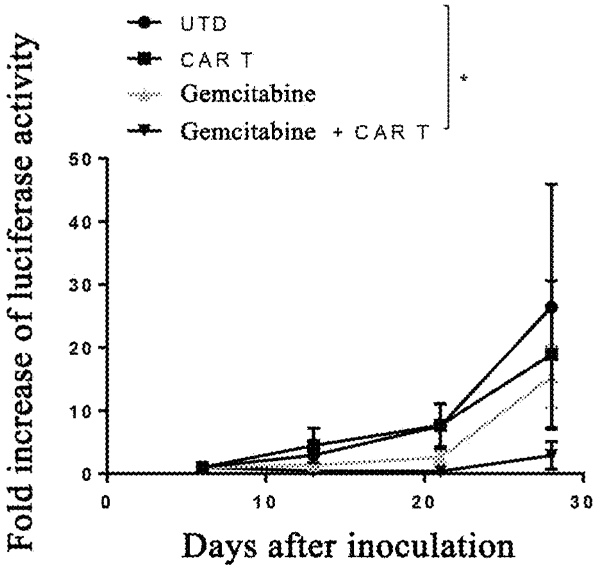
FIG. 3 shows the in vivo imaging data of mice treated with the combination of Gemcitabine and the CART cells.
Figure 4:
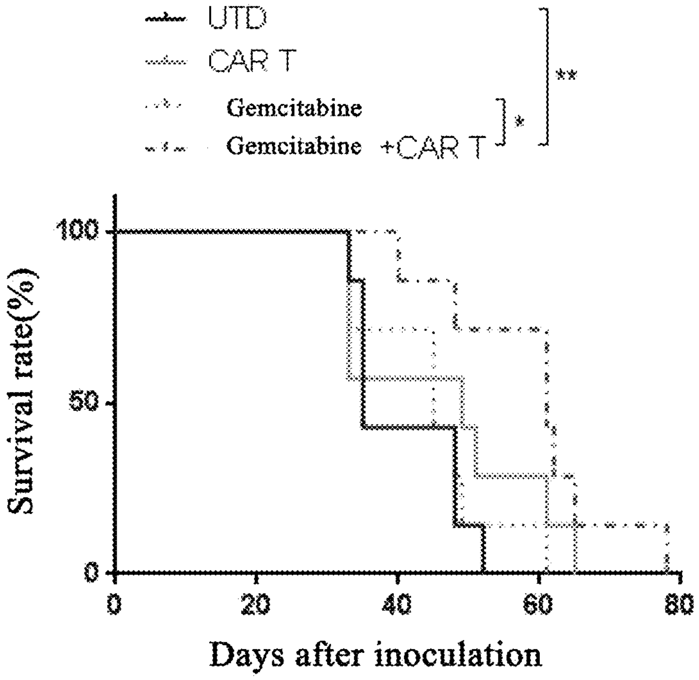
FIG. 4 shows the survival data of mice treated with the combination of Gemcitabine and CART cells.

The results of the inhibitory effect on mouse pancreatic cancer in situ are shown in FIG. 2. On the 13th day after receiving the treatment (Day 13), compared to the UTD group, CART group, and Gemcitabine group, the tumor burdens (white highlighted areas) in mice of Gemcitabine+CART group have significantly decreased, and two mice in the Gemcitabine+CART group show complete remission. On the 21st day (Day 21), in the Gemcitabine+CART group, four mice are with complete remission. For the other three groups, no mice with complete remission appear on the 21st day. In vivo imaging data shows that, the tumors of mice in the UTD group, CART group and Gemcitabine group continue to grow; compared with the UTD group, the tumor growth of the mice in the Gemcitabine+CART group is effectively controlled ($P<0.05$, FIG. 3). The survival data of mice shows that the survival period of mice in the Gemcitabine+CART group is the longest, which significantly exceed the survival period of mice in the UTD group ($P<0.01$, FIG. 4) and the survival period of mice in the Gemcitabine group ($P<0.05$, FIG. 4).

All documents mentioned in the present invention are cited as references in this application, as if each document is individually cited as a reference. In addition, it should be understood that after reading the above teaching content of the present invention, those skilled in the art can make various changes or modifications to the present invention, and these equivalent forms also fall within the scope defined by the appended claims of the present application.

The sequences involved in this application are as follows:

| Sequence number | Sequence name | Sequences |
|---|---|---|
| SEQ ID NO: 1 | murine CLD18.2 (nucleic acid sequence) | atgtcggtgaccgcc<br>tgccagggcuggggt<br>ttgtggtgtcactga<br>tcgggtttgcgggca<br>tcattgcagccactt<br>gtatggaccagtgga<br>gcacccaggatttat<br>acaacaacccggtga<br>ccgctgtattcaact<br>accaagggctatggc<br>gttcatgcgtccgag<br>agagctctggcttca<br>ccgagtgccgaggct<br>acttcaccctgttgg<br>ggttgccagccatgc<br>tgcaagctgtacgag<br>ccctgatgatcgtgg<br>gcattgttctggggg<br>tcatcggtatcctcg<br>tgtccatcttcgccc<br>tgaagtgcattcgca<br>ttggtagcatggatg<br>actctgccaaggcca<br>agatgactctgactt<br>ctgggatcttgttca<br>tcatctccggcatct<br>gtgcaatcattggtg<br>tgtctgtgtttgcca<br>acatgctggtgacca<br>acttctggatgtcca<br>cagctaacatgtaca<br>gcggcatgggcggca<br>tgggtggcatggtge<br>agaccgttcagacca |

-continued

| Sequence number | Sequence name | Sequences |
|---|---|---|
| | | ggtacacctttggtg<br>cagctctgttcgtgg<br>gctgggttgctggag<br>gcctcaccctgattg<br>ggggagtgatgatgt<br>gcatcgcctgccgtg<br>gcctgacaccagatg<br>acagcaacttcaaag<br>ctgtgtcttaccatg<br>cctctggccaaaatg<br>ttgcctacaggcctg<br>gaggctttaaggcca<br>gcactggctttgggt<br>ccaacaccagaaaea<br>agaagatctacgatg<br>ggggtgcccgcacag<br>aagacgatgaacagt<br>ctcatcctaccaagt<br>atgactatgtgtag |
| SEQ ID NO: 2 | human CLD18.2 (amino acid sequence) | MAVTACQGLGFVVSL<br>IGIAGIIAATCMDQW<br>STQDLYNNPVTAVFN<br>YQGLWRSCVRESSGF<br>TECRGYFTLLGLPAM<br>LQAVRALMIVGIVLG<br>AIGLLVSIFALKCIR<br>IGSMEDSAKANMTLT<br>SGIMFIVSGLCAIAG<br>VSVFANMLVTNFWMS<br>TANMYTGMGGMVQTV<br>QTRYTFGAALFVGWV<br>AGGLTLIGGVMMCIA<br>CRGLAPEETNYKAVS<br>YHASGHSVAYKPGGF<br>KASTGFGSNTKNKKI<br>YDGGARTEDEVQSYP<br>SKHDYV |
| SEQ ID NO: 3 | human CLD18.1 (amino acid sequence) | MSTTTCQWAFLLSIL<br>GLAGCIAATGMDMWS<br>TQDLYDNPVTSVFQY<br>EGLWRSCVRQSSGFT<br>ECRPYFTILGLPAML<br>QAVRALMIVGIVLGA<br>IGLLVSIFALKCIRI<br>GSMEDSAKANMTLTS<br>GIMFIVSGLCAIAGV<br>SVFANMLVTNFWMST<br>ANMYTGMGGMVQTVQ<br>TRYTFGAALFVGWVA<br>GGLTLIGGVMMCIAC<br>RGLAPEETNYKAVSY<br>HASGHSVAYKPGGFK<br>ASTGFGSNTKNKKIY<br>DGGARTEDEVQSYPS<br>KHDYV |
| SEQ ID NO: 4 | anti-CLD18.2 scfv (amino acid sequence 1) | QVQLQESGPGLIKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAIYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKR |

-continued

| Sequence number | Sequence name | Sequences |
|---|---|---|
| SEQ ID NO: 5 | anti-CLD18.2 scfv (nucleic acid sequence 1) | caggtgcagctgcag gagagcggccccggc ctgatcaagcccagc cagaccctgagcctg acctgcaccgtgagc ggcggcagcatcagc agcggctacaactgg cactggatccggcag ccccccggcaagggc ctggagtggatcggc tacatccactacacc g gcagcaccaactaca accccgccctgcgga gccgggtgaccatca gcgtggacaccagca agaaccagttcagcc tgaagctgagcagcg tgaccgccgccgaca ccgccatctactact gcgcccggatctaca acggcaacagcttcc cctactggggccagg gcaccaccgtgaccg tgagcagcggtggag gcggttcaggcggag gtggttctggcggtg gcggatcggacatcg tgatgacccagagcc ccgacagcctggccg tgagcctgggcgagc gggccaccatcaact gcaagagcagccaga gcctgttcaacagcg gcaaccagaagaact acctgacctggtacc agcagaagcccggcc agcccccccaagctgc tgatctactgggcca gcacccgggagagcg gcgtgcccgaccggt tcagcggcagcggca gcggcaccgacttca ccctgacattcagca gcctgcaggccgagg acgtggccgtgtact actgccagaacgcct acagcttcccctaca ccttcggcggcggca ccaagctggagatca agcgg |
| SEQ ID NO: 6 | murine CD8α signal peptide (amino acid sequence) | MASPLTRFLSLNLLL LGESIILGSGEA |
| SEQ ID NO: 7 | murine CD8α signal peptide (nucleic acid sequence) | atggcctcaccgttg acccgctttctgtcg ctgaacctgctgctg ctgggtgagtcgatt atcctggggagtgga gaagct |
| SEQ ID NO: 8 | murine CD8 hinge and transmembrane region (amino acid sequence) | TTTKPVLRTPSPVHP TGTSQPQRPEDCRPR GSVKGTGLDFACDIY IWAPLAGICVALLLS LIITLICYHRSR |
| SEQ ID NO: 9 | murine CDS hinge and transmembrane region (nucleic acid sequence) | actactaccaagcca gtgctgcgaactccc tcacctgtgcaccct accgggacatctcag ccccagagaccagaa gattgtcggccccgt ggetcagtgaagggg |

-continued

| Sequence number | Sequence name | Sequences |
|---|---|---|
| | | accggattggacttc gcctgtgatatttac atctgggcacccttg gccggaatctgcgtg gcccttctgctgtcc ttgatcatcactctc atctgctaccacagg agccga |
| SEQ ID NO: 10 | murine 4-IBB intracellular signaling domain (amino acid sequence) | KWIRKKFPHIFKQPF KKTTGAAQEEDACSC RCPQEEEGGGGGYEL |
| SEQ ID NO: 11 | murine 4-IBB intracellular signaling domain (nucleic acid sequence) | aaatggatcaggaaa aaattcccccacata ttcaagcaaccattt aagaagaccactgga gcagctcaagaggaa gatgcttgtagctgc cgatgtccacaggaa gaagaaggaggagga ggaggctatgagctg |
| SEQ ID NO: 12 | murine CD3 intracellular segment CD3ζ(amino acid sequence) | SRSAETAANLQDPNQ LYNELNLGRREEYDV LEKKRARDPEMGGKQ QRRRNPQEGVYNALQ KDKMAEAYSEIGTKG ERRRGKGHDGLYQGL STATKDTYDALHMQT LA |
| SEQ ID NO: 13 | murine CD3 intracellular segment CD3ζ(amino acid sequence) | agcaggagtgcagag actgctgccaacctg caggaccccaaccag ctctacaatgagctc aatctagggcgaaga gaggaatatgacgtc ttggagaagaagcgg gctcgggatccagag atgggaggcaaacag cagaggaggaggaac ccccaggaaggcgta tacaatgcactgcag aaagacaagatggca gaagcctacagtgag atcggcacaaaaggc gagaggcggagaggc aaggggcacgatggc ctttaccagggtctc agcactgccaccaag gacacctatgatgcc ctgcatatgcagacc ctggcc |
| SEQ ID NO: 14 | anti-CLD18.2 scfv (amino acid sequence 2) | QVQLQQSGAELARPG ASVKMSCKASGYTFT SYTMHWVKQRPGQGL EWIGYINPSSGYTNY NQKFKDKATLTADKS SSTAYMQLSSLTSED SAVYYCARIYYGNSF AYWGQGTTVTVSSGG GGSGGGGSGGGGSDI VMTQSPSSLTVTAGE KVTMSCKSSQSLLNS GNQKNYLTWYQQKPG QPPKLLIYWASTRES GVPDRFTGSGSGTDF TLTISSVQAEDL AVYYCQNDYSYPLTF GAGTKLELKR |

-continued

| Sequence number | Sequence name | Sequences |
|---|---|---|
| SEQ ID NO: 15 | anti-CLD18.2 scfv (amino acid sequence 3) | QVQLQQSGPELVKPG<br>ALVKISCKASGYTFT<br>SYDINWVKQRPGQGL<br>EWIGWIYPGDGSTKY<br>NEKFKGKATLTADKS<br>SSTAYMQLSSLTSEN<br>SAVYFCARGGYRYDE<br>AMDYWGQGTTVTVSS<br>GGGGSGGGGSGGGGS<br>QIVLTQSPAIMSASP<br>GEKVTMTCSASSSIS<br>YMHWYQQKPGTSPKR<br>WIYDTSKLASGVPAR<br>FSGSGSGTSYSLTIS<br>SMEAEDAATYYCHQR<br>SSYPYTFGGGTKLEI<br>KR |
| SEQ ID NO: 16 | anti-CLD18.2 scfv (amino acid sequence 4) | QIQLVQSGPELKKPG<br>ETVKISCKASGYTFT<br>NYGMNWVKQAPGKGL<br>KWMGWINTNTGEPTY<br>AEEFKGRFAFSLETS<br>ASTAYLQINNLKNED<br>TATYFCARFSYGNSF<br>AYWGQGTTVTVSSGG<br>GGSGGGGSGGGGSDI<br>VMTQSPSSLSVSAGE<br>KVTMSCKSSQSLLNS<br>GNQKNYLAWYQQKPG<br>QPPKLLIYGASTRES<br>GVPDRFTGSGSGTDF<br>TLTISSVQAEDLAVY<br>YCQNDHSYPLTFGAG<br>TKLELKR |
| SEQ ID NO: 17 | anti-CLD18.2 scfv (amino acid sequence 5) | DVQLQESGPDLVKPS<br>QSLSLTCTVTGYSIT<br>SGYNWHWIRQFPGNK<br>MEWMGYIHYTGSTNY<br>NPSLRSRISITRDTS<br>KNQFFLQLNSVTTDD<br>TATYYCTRIYNGNSF<br>PYWGQGTSVTVSSGG<br>GGSGGGGSGGGGSDI<br>VMTQSPSSLTVTPGE<br>KVTMTCKSSQSLFNS<br>GNQKNYLTWYQQRPG<br>QPPKMLIYWASTRES<br>GVPDRFTGSGSGTDF<br>TLTISSVQAEDLAVF<br>YCQNAYSFPYTFGGG<br>TKLEIKR |
| SEQ ID NO: 18 | anti-CLD18.2 scfv (amino acid sequence 6) | QVQLQQSGAELARPG<br>ASVKMSCKASGYTFT<br>SYTMHWVKQRPGQGL<br>EWIGYIDPSSGYTNY<br>NQKFKDKATLTADKS<br>SSTAYMQLSSLTSED<br>SAVYYCARIYYGNSF<br>AYWGQGTTVTVSSGG<br>GGSGGGGSGGGGSDI<br>VMTQSPSSLTVTAGE<br>KVTMSCKSSQSLLNS<br>GNQKNYLTWYQQKPG<br>QPPKLLIYWASTRES<br>GVPDRFTGSGSGTDF<br>TLTISSVQAEDLAVY<br>YCQNDYSYPLTFGAG<br>TKLELKR |
| SEQ ID NO: 19 | anti-CLD18.2 scfv (amino acid sequence 7) | QVQLQQSGAELARPG<br>ASVKMSCKASGYTFT<br>SYTMHWVKQRPGQGL<br>EWIGYINPASGYTNY<br>NQKFKDKATLTADKS<br>SSTAYMQLSSLTSED<br>SAVYYCARIYYGNSF<br>AYWGQGTTVTVSSGG<br>GGSGGGGSGGGGSDI<br>VMTQSPSSLTVTAGE<br>KVTMSCKSSQSLLNS<br>GNQKNYLTWYQQKPG<br>QPPKLLIYWASTRES<br>GVPDRFTGSGSGTDF<br>TLTISSVQAEDLAVY<br>YCQNDYSYPLTFGAG<br>TKLELKR |
| SEQ ID NO: 20 | anti-CLD18.2 scfv (amino acid sequence 8) | QVQLQQSGAELARPG<br>ASVKMSCKASGYTFT<br>SYTMHWVKQRPGQGL<br>EWIGYINPASGYTNY<br>NQKFKDKATLTADKS<br>SSTAYMQLSSLTSED<br>SAVYYCARIYYGNSF<br>AYWGQGTTVTVSSGG<br>GGSGGGGSGGGGSDI<br>VMTQSPSSLTVTAGE<br>KVTMSCKSSQSLLNS<br>GNQKNYLTWYQQKPG<br>QPPKLLIYWASTRES<br>GVPDRFTGSGSGTDF<br>TLTISSVQAEDLAVY<br>YCQNDYSYPLTFGAG<br>TKLELKR |
| SEQ ID NO: 21 | anti-CLD18.2 scfv (amino acid sequence 9) | QVQLVQSGAEVKKPG<br>ASVKVSCKASGYTFT<br>SYTMHWVRQAPGQGL<br>EWMGYINPASGYTNY<br>NQKFKDRVTMTRDTS<br>TSTAYMELSSLRSED<br>TAVYYCARIYYGNSF<br>AYWGQGTLVTVSSGG<br>GGSGGGGSGGGGSDI<br>VMTQSPDSLAVSLGE<br>RATINCKSSQSLLNS<br>GNQKNYLTWYQQKPG<br>QPPKLLIYWASTRES<br>GVPDRFSGSGSGTDF<br>TLTISSLQAEDVAVY<br>YCQNDYSYPLTFGGG<br>TKVEIKR |
| SEQ ID NO: 22 | anti-CLD18.2 scfv (amino acid sequence 10) | QVQLQESGPGLVKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAVYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKR |
| SEQ ID NO: 23 | chimeric antigen receptor 1 | QVQLQQSGAELARPG<br>ASVKLSCKASGYTFT<br>DYYINWVKQRTGQGL<br>EWIGEIYPGSGNTYY<br>NEKFKGKATLTADKS<br>SSTAYMQLSSLTSED<br>SAVYFCARSYGAFDY<br>WGQGT |

-continued

| Sequence number | Sequence name | Sequences |
|---|---|---|
| | | TLTVSSGGGGSGGGG<br>SGGGGSDIVMTQSQK<br>FMSTSVGDRVSITCK<br>ASQNVRTAVAWYQQK<br>PGQSPKALIYLASNR<br>HTGVPDRFTGSGSGT<br>DFTLTISNVQSEDLA<br>DYFCLQHWNYPLTFG<br>GGTKLEIKRTTTPAP<br>RPPTPAPTIASQPLS<br>LRPEACRPAAGGAVH<br>TRGLDFACDFWVLVV<br>VGGVLACYSLLVTVA<br>FIIFWVRSKRSRLLH<br>SDYMNMTPRRPGPTR<br>KHYQPYAPPRDFAAY<br>RSRVKFSRSADAPAY<br>QQGQNQLYNELNLGR<br>REEYDVLDKRRGRDP<br>EMGGKPQRRKNPQEG<br>LYNELQKDKMAEAYS<br>EIGMKGERRRGKGHD<br>GLYQGLSTATKDTYD<br>ALHMQALPPR |
| SEQ ID NO: 24 | chimeric antigen receptor 2 | QVQLQQSGAELARPG<br>ASVKLSCKASGYTFT<br>DYYINWVKQRTGQGL<br>EWIGEIYPGSGNTYY<br>NEKFKGKATLTADKS<br>SSTAYMQLSSLTSED<br>SAVYFCARSYGAFDY<br>WGQGTTLTVSSGGGG<br>SGGGGSGGGGSDIVM<br>TQSQKFMSTSVGDRV<br>SITCKASQNVRTAVA<br>WYQQKPGQSPKALIY<br>LASNRHTGVPDRFTG<br>SGSGTDFTLTISNVQ<br>SEDLADYFCLQHWNY<br>PLTFGGGTKLEIKRT<br>TTPAPRPPTPAPTIA<br>SQPLSLRPEACRPAA<br>GGAVHTRGLDFACDI<br>YIWAPLAGTCGVLLL<br>SLVITLYCKRGRKKL<br>LYIFKQPFMRPVQTT<br>QEEDGCSCRFPEEEE<br>GGCELRVKFSRSADA<br>PAYKQGQNQLYNELN<br>LGRREEYDVLDKRRG<br>RDPEMGGKPRRKNPQ<br>EGLYNELQKDKMAEA<br>YSEIGMKGERRRGKG<br>HDGLYQGLSTATKDT<br>YDALHMQALPPR |
| SEQ ID NO: 25 | chimeric antigen receptor 3 | QVQLQQSGAELARPG<br>ASVKLSCKASGYTFT<br>DYYINWVKQRTGQGL<br>EWIGEIYPGSGNTYY<br>NEKFKGKATLTADKS<br>SSTAYMQLSSLTSED<br>SAVYFCARSYGAFDY<br>WGQGTTLTVSSGGGG<br>SGGGGSGGGGSDIVM<br>TQSQKFMSTSVGDRV<br>SITCKASQNVRTAVA<br>WYQQKPGQSPKALIY<br>LASNRHTGVPDRFTG<br>SGSGTDFTLTISNVQ<br>SEDLADYFCLQHWNY<br>PLTFGGGTKLEIKRT<br>TTPAPRPPTPAPTIA<br>SQPLSLRPEACRPAA<br>GGAVHTRGLDFACDF |

-continued

| Sequence number | Sequence name | Sequences |
|---|---|---|
| | | WVLWVGGVLACYSLL<br>VTVAFIIFWVRSKRS<br>RLLHSDYMNMTPRRP<br>GPTRKHYQPYAPPRD<br>FAAYRSKRGRKKLLY<br>IFKQPFMRPVQTTQE<br>EDGCSCRFPEEEEGG<br>CELRVKFSRSADAPA<br>YQQGQNQLYNELNLG<br>RREEYDVLDKRRGRD<br>PEMGGKPQRRKNPQE<br>GLYNELQKDKMAEAY<br>SEIGMKGERRRGKGH<br>DGLYQGLSTATKDTY<br>DALHMQALPPR |
| SEQ ID NO: 26 | chimeric antigen receptor 4 | QIQLVQSGPELKKPG<br>ETVKISCKASGYTFT<br>NYGMNWVKQAPGKGL<br>KWMGWINTNTGEPTY<br>AEEFKGRFAFSLETS<br>ASTAYLQINNLKNED<br>TATYFCARLGFGNAM<br>DYWGQGTSVTVSSGG<br>GGSGGGGSGGGGSDI<br>VMTQSPSSLTVTAGE<br>KVTMSCKSSQSLLNS<br>GNQKNYLTWYQQKPG<br>QPPKLLIYWASTRES<br>GVPDRFTGSGSGTDF<br>TLTISSVQAEDLAVY<br>YCQNDYSYPLTFGAG<br>TKLELKRTTTPAPRP<br>PTPAPTIASQPLSLR<br>PEACRPAAGGAVHTR<br>GLDFACDFWVLVVVG<br>GVLACYSLLVTVAFU<br>FWVRSKRSRLLHSDY<br>MNMTPRRPGPTRKHY<br>QPYAPPRDFAAYRSR<br>VKFSRSADAPAYQQG<br>QNQLYNELNLGRREE<br>YDVLDKRRGRDPEMG<br>GKPQRRKNPQEGLYN<br>ELQKDKMAEAYSEIG<br>MKGERRRGKGHDGLY<br>QGLSTATKDTYDALH<br>MQALPPR |
| SEQ ID NO: 27 | chimeric antigen receptor 5 | QIQLVQSGPELKKPG<br>ETVKISCKASGYTFT<br>NYGMNWVKQAPGKGL<br>KWMGWINTNTGEPTY<br>AEEFKGRFAFSLETS<br>ASTAYLQINNLKNED<br>TATYFCARLGFGNAM<br>DYWGQGTSVTVSSGG<br>GGSGGGGSGGGGSDI<br>VMTQSPSSLTVTAGE<br>KVTMSCKSSQSLLNS<br>GNQKNYLTWYQQKPG<br>QPPKLLIYWASTRES<br>GVPDRFTGSGSGTDF<br>TLTISSVQAEDLAVY<br>YCQNDYSYPLTFGAG<br>TKLELKRTTTPAPRP<br>PTPAPTIASQPLSLR<br>PEACRPAAGGAVHTR<br>GLDFACDIYIWAPLA<br>GTCGVLLLSLVITLY<br>CKRGRKKLLYIFKQP<br>FMRPVQTTQEEDGCS<br>CRFPEEEEGGCELRV<br>KFSRSADAPAYKQGQ<br>NQLYNELNLGRREEY<br>DVLDKRRGRDPEMGG |

-continued

| Sequence number | Sequence name | Sequences |
|---|---|---|
| | | KPRRKNPQEGLYNEL QKDKMAEAYSEIGMK GERRRGKG HDGLYQGLSTATKDT YDALHMQALPPR |
| SEQ ID NO: 28 | chimeric antigen receptor 6 | QIQLVQSGPELKKPG ETVKISCKASGYTFT NYGMNWVKQAPGKGL KWMGWINTNTGEPTY AEEFKGRFAFSLETS ASTAYLQINNLKNED TATYFCARLGFGNAM DYWGQGTSVTVSSGG GGSGGGGSGGGGSDI VMTQSPSSLTVTAGE KVTMSCKSSQSLLNS GNQKNYLTWYQQKPG QPPKLLIYWASTRES GVPDRFTGSGSGTDF TLTISSVQAEDLAVY YCQNDYSYPLTFGAG TKLELKRTTTPAPRP PTPAPTIASQPLSLR PEACRPAAGGAVHTR GLDFACDFWVLWVGG VLACYSLLVTVAFIT FWVRSKRSRLLHSDY MNMTPRRPGPTRKHY QPYAPPRDFAAYRSK RGRKKLLYIFKQPFM RPVQTTQEEDGCSCR FPEEEEGGCELRVKF SRSADAPAYQQGQNQ LYNELNLGRREEYDV LDKRRGRDPEMGGKP QRRKNPQEGLYNELQ KDKMAEAYSEIGMKG ERRRGKGHDGLYQGL STATKDTYDALHMQA LPPR |
| SEQ ID NO: 29 | chimeric antigen receptor 7 | QVQLQQPGAELVRPG ASVKLSCKASGYTFT SYWINWVKQRPGQGL EWIGNIYPSDSYTNY NQKFKDKATLTVDKS SSTAYMQLSSPTSED SAVYYCTRSWRGNSF DYWGQGTTLTVSSGG GGSGGGGSGGGGSDI VMTQSPSSLTVTAGE KVTMSCKSSQSLLNS GNQKNYLTWYQQKPG QPPKLLIYWASTRES GVPDRFTGSGSGTDF TLTISSVQAEDLAVY YCQNDYSYPFTFGSG TKLEIKTTTPAPRPP TPAPTIASQPLSLRP EACRPAAGGAVHTRG LDFACDFWVLVVVGG VLACYSLLVTVAFII FWVRSKRSRLLHSDY MNMTPRRPGPTRKHY QPYAPPRDFAAYRSR VKFSRSADAPAYQQG QNQLYNELNLGRREE YDVLDKRRGRDPEMG GKPQRRKNPQEGLYN ELQKDKMAEAYSEIG MKGERRRGKGHDGLY QGLSTATKDTYDALH MQALPPR |

-continued

| Sequence number | Sequence name | Sequences |
|---|---|---|
| SEQ ID NO: 30 | chimeric antigen receptor 8 | QVQLQQPGAELVRPG ASVKLSCKASGYTFT SYWINWVKQRPGQGL EWIGNIYPSDSYTNY NQKFKDKATLTVDKS SSTAYMQLSSPTSED SAVYYCTRSWRGNSF DYWGQGTTLTVSSGG GGSGGGGSGGGGSDI VMTQSPSSLTVTAGE KVTMSCKSSQSLLNS GNQKNYLTWYQQKPG QPPKLLIYWASTRES GVPDRFTGSGSGTDF TLTISSVQAEDLAVY YCQNDYSYPFTFGSG TKLEIKTTTPAPRPP TPAPTIASQPLSLRP EACRPAAGGAVHTRG LDFACDIYIWAPLAG TCGVLLLSLVTTLYC KRGRKKLLYIFKQPF MRPVQTTQEEDGCSC RFPEEEEGGCELRVK FSRSADAPAYKQGQN QLYNELNLGRREEYD VLDKRRGRDPEMGGK PRRKNPQEGLYNELQ KDKMAEAYSEIGMKG ERRRGKGHDGLYQGL STATKDTYDALHMQA LPPR |
| SEQ ID NO: 31 | chimeric antigen receptor 9 | QVQLQQPGAELVRPG ASVKLSCKASGYTFT SYWINWVKQRPGQGL EWIGNIYPSDSYTNY NQKFKDKATLTVDKS SSTAYMQLSSPTSED SAVYYCTRSWRGNSF DYWGQGTTLTVSSGG GGSGGGGSGGGGSDI VMTQSPSSLTVTAGE KVTMSCKSSQSLLNS GNQKNYLTWYQQKPG QPPKLLIYWASTRES GVPDRFTGSGSGTDF TLTISSVQAEDLAVY YCQNDYSYPFTFGSG TKLEIKTTTPAPRPP TPAPTIASQPLSLRP EACRPAAGGAVHTRG LDFACDFWVLVVVGG VLACYSLLVTVAFII FWVRSKRSRLLHSDY MNMTPRRPGPTRKHY QPYAPPRDFAAYRSK RGRKKLLYIFKQPFM RPVQTTQEEDGCSCR FPEEEEGGCELRVKF SRSADAPAYQQGQNQ LYNELNLGRREEYDV LDKRRGRDPEMGGKP QRRKNPQEGLYNELQ KDKMAEAYSEIGMKG ERRRGKGHDGLYQGL STATKDTYDALHMQA LPPR |
| SEQ ID NO: 32 | chimeric antigen receptor 10 | QVQLQQSGAELARPG ASVKMSCKASGYTFT SYTMHWVKQRPGQGL EWIGYINPASGYTNY NQKFKDKATLTADKS SSTAYMQLSSLTSED SAVYYCARIYYGNSF |

-continued

| Sequence number | Sequence name | Sequences |
|---|---|---|
| | | AYWGQGTTVTVSSGGGGSGGGGSGGGGSDIVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLELKRTTTPAPRPPTPAPTIASQPLSLRPEACRPAAGGAVHTRGLDFACDFWVLVWGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| SEQ ID NO: 33 | chimeric antigen receptor 11 | QVQLQQSGAELARPGASVKMSCKASGYTFTSYTMHWVKQRPGQGLEWIGYINPASGYTNYNQKFKDKATLTADKSSSTAYMQLSSLTSEDSAVYYCARIYYGNSFAYWGQGTTVTVSSGGGGSGGGGSGGGGSDIVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLELKRTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| SEQ ID NO: 34 | chimeric antigen receptor 12 | QVQLQQSGAELARPGASVKMSCKASGYTFTSYTMHWVKQRPGQGLEWIGYINPASGYTNYNQKFKDKATLTADKSSSTAYMQLSSLTSEDSAVYYCARIYYGNSFAYWGQGTTVTVSSGGGGSGGGGSGGGGSDIVMTQSPSSLTVTAGEKVTMSCKSSQSLLNSGNQKNYLTWYQQKPGQPPKLLIYWASTRESGVPDRFTGSGSGTDFTLTISSVQAEDLAVYYOQNDYSYPLTFGAGTKLELKRTTTPAPRP |

-continued

| Sequence number | Sequence name | Sequences |
|---|---|---|
| | | PTPAPTIASQPLSLRPEACRPAAGGAVHTRGLDFACDFWVLVVVGGVLACYSLLVTVAFIIFWVRSKRSRLLHSDYMNMTPRRPGPTRKHYQPYAPPRDFAAYRSKRGRKKLLYIFKQPFMRPVQTTQEEDGCSCRFPEEEEGGCELRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| SEQ ID NO: 35 | chimeric antigen receptor 13 | QVQLVQSGAEVKKPGASVKVSCKASGYTFTSYTMHWVRQAPGQGLEWMGYINPASGYTNYNQKFKDRVTMTRDTSTSTAYMELSSLRSEDTAVYYCARIYYGNSFAYWGQGTLVTVSSGGGGSGGGGSGGGGSDIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYSYPLTFGGGTKVEIKRTTTPAPRPPTPAPTIASQPLSLRPEACRPAAGGAVHTRGLDFACDFWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| SEQ ID NO: 36 | chimeric antigen receptor 14 | QVQLVQSGAEVKKPGASVKVSCKASGYTFTSYTMHWVRQAPGQGLEWMGYINPASGYTNYNQKFKDRVTMTRDTSTSTAYMELSSLRSEDTAVYYCARIYYGNSFAYWGQGTLVTVSSGGGGSGGGGSGGGGSDIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYSYPLTFGGGTKVEIKRTTTPAPRPPTPAPTIASQPLSLRPEACRPAAGGAVHTRGLDFACDIYIWAPLAGTCGVLLLSLVITLYCKRGRKKLLYIFKQPFMRP VQTTQEEDGCSCRFP |

-continued

| Sequence number | Sequence name | Sequences |
|---|---|---|
| | | EEEEGGCELRVKFSR<br>SADAPAYKQGQNQLY<br>NELNLGRREEYDVLD<br>KRRGRDPEMGGKPRR<br>KNPQEGLYNELQKDK<br>MAEAYSEIGMKGERR<br>RGKGHDGLYQGLSTA<br>TKDTYDALHMQALPP<br>R |
| SEQ ID NO: 37 | chimeric antigen receptor 15 | QVQLVQSGAEVKKPG<br>ASVKVSCKASGYTFT<br>SYTMHWVRQAPGQGL<br>EWMGYINPASGYTNY<br>NQKFKDRVTMTRDTS<br>TSTAYMELSSLRSED<br>TAVYYCARIYYGNSF<br>AYWGQGTLVTVSSGG<br>GGSGGGGSGGGGSDI<br>VMTQSPDSLAVSLGE<br>RATINCKSSQSLLNS<br>GNQKNYLTWYQQKPG<br>QPPKLLIYWASTRES<br>GVPDRFSGSGSGTDF<br>TLTISSLQAEDVAVY<br>YCQNDYSYPLTFGGG<br>TKVEIKRTTTPAPRP<br>PTPAPTIASQPLSLR<br>PEACRPAAGGAVHTR<br>GLDFACDFWVLVVVG<br>GVLACYSLLVTVAFI<br>IFWVRSKRSRLLHSD<br>YMNMTPRRPGPTRKH<br>YQPYAPPRDFAAYRS<br>KRGRKKLLYIFKQPF<br>MRPVQTTQEEDGCSC<br>RFPEEEEGGCELRVK<br>FSRSADAPAYQQGQN<br>QLYNELNLGRREEYD<br>VLDKRRGRDPEMGGK<br>PQRRKNPQEGLYNEL<br>QKDKMAEAYSEIGMK<br>GERRRGKGHDGLYQG<br>LSTATKDTYDALHMQ<br>ALPPR |
| SEQ ID NO: 38 | chimeric antigen receptor 16 | QVQLQESGPGLVKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAVYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKRTTTPAPRP<br>PTPAPTIASQPLSLR<br>PEACRPAAGGAVHTR<br>GLDFACDFWVLVVVG<br>GVLACYSLLVTVAFI<br>IFWVRSKRSRLLHSD<br>YMNMTPRRPGPTRKH<br>YQPYAPPRDFAAYRS<br>RVKFSRSADAPAYQQ<br>GQNQLYNELNLGRRE<br>EYDVLDKRRGRDPEM |
| | | GGKPQRRKNPQEGLY<br>NELQKDKMAEAYSEI<br>GMKGERRRGKGHDGL<br>YQGLSTATKDTYDAL<br>HMQALPPR |
| SEQ ID NO: 39 | chimeric antigen receptor 17 | QVQLQESGPGLVKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAVYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKRTTTPAPRP<br>PTPAPTIASQPLSLR<br>PEACRPAAGGAVHTR<br>GLDFACDIYIWAPLA<br>GTCGVLLLSLVITLY<br>CKRGRKKLLYIFKQP<br>FMRPVQTTQEEDGCS<br>CRFPEEEEGGCELRV<br>KFSRSADAPAYKQGQ<br>NQLYNELNLGRREEY<br>DVLDKRRGRDPEMGG<br>KPRRKNPQEGLYNEL<br>QKDKMAEAYSEIGMK<br>GERRRGKGHDGLYQG<br>LSTATKDTYDALHMQ<br>ALPPR |
| SEQ ID NO: 40 | chimeric antigen receptor 18 | QVQLQESGPGLVKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAVYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKRTTTPAPRP<br>PTPAPTIASQPLSLR<br>PEACRPAAGGAVHTR<br>GLDFACDFWVLVVVG<br>GVLACYSLLVTVAFI<br>IFWVRSKRSRLLHSD<br>YMNMTPRRPGPTRKH<br>YQPYAPPRDFAAYRS<br>KRGRKKLLYIFKQPF<br>MRPVQTTQEEDGCSC<br>RFPEEEEGGCELRVK<br>FSRSADAPAYQQGQN<br>QLYNELNLGRREEYD<br>VLDKRRGRDPEMGGK<br>PQRRKNPQEGLYNEL<br>QKDKMAEAYSEIGMK<br>GERRRGKGHDGLYQG<br>LSTATKDTYDALHMQ<br>ALPPR |

-continued

| Sequence number | Sequence name | Sequences |
|---|---|---|
| SEQ ID NO: 41 | chimeric antigen receptor 19 | QVQLQESGPGLIKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAIYYCARIYNGNSF<br>PYWGQGTT<br>VTVSSGGGGSGGGGS<br>GGGGSDIVMTQSPDS<br>LAVSLGERATINCKS<br>SQSLFNSGNQKNYLT<br>WYQQKPGQPPKLLIY<br>WASTRESGVPDRFSG<br>SGSGTDFTLTISSLQ<br>AEDVAVYYCQNAYSF<br>PYTFGGGTKLEIKRT<br>TTPAPRPPTPAPTIA<br>SQPLSLRPEACRPAA<br>GGAVHTRGLDFACDF<br>WVLVVVGGVLACYSL<br>LVTVAFIIFWVRSKR<br>SRLLHSDYMNMTPRR<br>PGPTRKHYQPYAPPR<br>DFAAYRSRVKFSRSA<br>DAPAYQQGQNQLYNE<br>LNLGRREEYDVLDKR<br>RGRDPEMGGKPQRRK<br>NPQEGLYNELQKDKM<br>AEAYSEIGMKGERRR<br>GKGHDGLYQGLSTAT<br>KDTYDALHMQALPPR |
| SEQ ID NO: 42 | chimeric antigen receptor 20 | QVQLQESGPGLIKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAIYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKRTTTPAPRP<br>PTPAPTIASQPLSLR<br>PEACRPAAGGAVHTR<br>GLDFACDIYIWAPLA<br>GTCGVLLLSLVITLY<br>CKRGRKKLLYIFKQP<br>FMRPVQTTQEEDGCS<br>CRFPEEEEGGCELRV<br>KFSRSADAPAYKQGQ<br>NQLYNELNLGRREEY<br>DVLDKRRGRDPEMGG<br>KPRRKNPQEGLYNEL<br>QKDKMAEAYSEIGMK<br>GERRRGKGHDGLYQG<br>LSTATKDTYDALHMQ<br>ALPPR |
| SEQ ID NO: 43 | chimeric antigen receptor 21 | QVQLQESGPGLIKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAIYYCARIYNGNSF<br>PYWGQGTTVTVSSGG<br>GGSGGGGSGGGGSDI<br>VMTQSPDSLAVSLGE |

-continued

| Sequence number | Sequence name | Sequences |
|---|---|---|
| | | RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKRTTTPAPRP<br>PTPAPTIASQPLSLR<br>PEACRPAAGGAVHTR<br>GLDFACDFWVLVVVG<br>GVLACYSLLVTVAFI<br>IFWVRSKRSRLLHSD<br>YMNMTPRRPGPTRKH<br>YQPYAPPRDFAAYRS<br>KRGRKKLLYIFKQPF<br>MRPVQTTQEEDGCSC<br>RFPEEEEGGCELRVK<br>FSRSADAPAYQQGQN<br>QLYNELNLGRREEYD<br>VLDKRRGRDPEMGGK<br>PQRRKNPQEGLYNEL<br>QKDKMAEAYSEIGMK<br>GERRRGKGHDGLYQG<br>LSTATKDTYDALHMQ<br>ALPPR |
| SEQ ID NO: 44 | chimeric antigen receptor 22 | QVQLQESGPGLIKPS<br>QTLSLTCTVSGGSIS<br>SGYNWHWIRQPPGKG<br>LEWIGYIHYTGSTNY<br>NPALRSRVTISVDTS<br>KNQFSLKLSSVTAAD<br>TAIYYCARIYNGNSF<br>PYWGQGTTVTVSSGG<br>GGSGGGGSGGGGSDI<br>VMTQSPDSLAVSLGE<br>RATINCKSSQSLFNS<br>GNQKNYLTWYQQKPG<br>QPPKLLIYWASTRES<br>GVPDRFSGSGSGTDF<br>TLTISSLQAEDVAVY<br>YCQNAYSFPYTFGGG<br>TKLEIKRTTTKPVLR<br>TPSPVHPTGTSQPQR<br>PEDCRPRGSVKGTGL<br>DFACDIYIWAPLAGI<br>CVALLLSLIITLICY<br>HRSRKWIRKKFPHIF<br>KQPFKKTTGAAQEED<br>ACSCRCPQEEEGGGG<br>GYELSRSAETAANLQ<br>DPNQLYNELNLGRRE<br>EYDVLEKKRARDPEM<br>GGKQQRRRNPQEGVY<br>NALQKDKMAEAYSEI<br>GTKGERRRGKGHDGL<br>YQGLSTATKDTYDAL<br>HMQTLA |

The invention claimed is:

1. A method for treating a tumor or reducing the growth, survival or viability of a cancer cell, wherein an immune effector cell and Gemcitabine are administered to an individual suffering from the tumor, wherein the immune effector cell expresses a receptor recognizing a tumor antigen, wherein the tumor antigen is Claudin18.2.

2. The method of claim 1, wherein the method of administering the immune effector cell and Gemcitabine to an individual suffering from the tumor is selected from any one of the following:

(1) firstly administering Gemcitabine and then the immune effector cell, (2) simultaneously administering the immune effector cell and Gemcitabine, and (3) firstly administering the immune effector cell and then Gemcitabine.

3. The method of claim 1, wherein the receptor is selected from: Chimeric Antigen Receptor (CAR), T cell receptor (TCR), T cell fusion protein (TFP), T cell antigen coupler (TAC), or a combination thereof.

4. The method of claim 3, wherein the chimeric antigen receptor comprises:

(i) an antibody recognizing Claudin 18.2 or a fragment thereof, the transmembrane region of CD28 or CD8, the costimulatory signal domain of CD28, and CD3ζ; or (ii) an antibody recognizing Claudin 18.2 or a fragment thereof, the transmembrane region of CD28 or CD8, the costimulatory signal domain of CD137, and CD3ζ; or (iii) an antibody recognizing Claudin 18.2 or a fragment thereof, the transmembrane region of CD28 or CD8, the costimulatory signal domain of CD28, the costimulatory signal domain of CD137, and CD3ζ.

5. The method of claim 4, wherein the amino acid sequence of the antibody recognizing Claudin 18.2 has at least 90% identity with an amino acid sequence shown in any one of SEQ ID NO: 4 and SEQ ID NOs: 14-22.

6. The method of claim 4, wherein the amino acid sequence of the chimeric antigen receptor has at least 90% identity with an amino acid sequence shown in any one of SEQ ID NOs: 23-44.

7. The method of claim 1, wherein, the tumor is selected from the group consisting of breast cancer, colon cancer, rectal cancer, renal cell carcinoma, liver cancer, lung cancer, small intestine cancer, esophageal cancer, melanoma, bone cancer, pancreatic cancer, skin cancer, head and neck cancer, uterine cancer, ovarian cancer, rectal cancer, gastric cancer, testicular cancer, uterine cancer, fallopian tube cancer, endometrial cancer, cervical cancer, vaginal cancer, thyroid cancer, parathyroid cancer, adrenal cancer, soft tissue sarcoma, urethral cancer, penile cancer, bladder cancer, ureteral cancer, renal pelvis cancer, spinal tumor, glioma, pituitary adenoma, Kaposi's sarcoma, a combination of any of the above cancers and metastatic lesions of the above cancers.

8. The method of claim 1, wherein the immune effector cell is selected from the group consisting of: T cell, B cell, natural killer (NK) cell, natural killer T (NKT) cell, mast cell, neutrophils, dendritic cell, bone marrow-derived phagocytic cell, and a combination thereof.

9. The method of claim 1, wherein Gemcitabine is administered by oral administration, intraperitoneal administration and/or injection.

10. The method of claim 1, wherein lymphocyte clearance is not performed on the individual.

11. The method of claim 5, wherein the amino acid sequence of the antibody recognizing Claudin 18.2 is an amino acid sequence shown in any one of SEQ ID NO: 4 and SEQ ID NOs: 14-22.

12. The method of claim 6, wherein the amino acid sequence of the chimeric antigen receptor is an amino acid sequence shown in any one of SEQ ID NOs: 23-44.

13. The method of claim 8, wherein the immune effector cell is selected from the group consisting of autologous T cell, allogeneic T cell, and allogeneic NK cell.

* * * * *

SEQUENCE LISTING

<160> NUMBER OF SEQ ID NOS: 44

<210> SEQ ID NO 1
<211> LENGTH: 795
<212> TYPE: DNA
<213> ORGANISM: Artificial Sequence
<220> FEATURE:
<223> OTHER INFORMATION: Description of Artificial Sequence: artificially synthesized sequence

<400> SEQUENCE: 1

```
atgtcggtga ccgcctgcca gggcttgggg tttgtggtgt cactgatcgg gtttgcgggc     60

atcattgcag ccacttgtat ggaccagtgg agcacccagg atttatacaa caacccggtg    120

accgctgtat tcaactacca agggctatgg cgttcatgcg tccgagagag ctctggcttc    180

accgagtgcc gaggctactt caccctgttg gggttgccag ccatgctgca agctgtacga    240

gccctgatga tcgtgggcat tgttctgggg gtcatcggta tcctcgtgtc catcttcgcc    300

ctgaagtgca ttcgcattgg tagcatggat gactctgcca aggccaagat gactctgact    360

tctgggatct tgttcatcat ctccggcatc tgtgcaatca ttggtgtgtc tgtgtttgcc    420

aacatgctgg tgaccaactt ctggatgtcc acagctaaca tgtacagcgg catgggcggc    480

atgggtggca tggtgcagac cgttcagacc aggtacacct ttggtgcagc tctgttcgtg    540

ggctgggttg ctggaggcct caccctgatt gggggagtga tgatgtgcat cgcctgccgt    600

ggcctgacac cagatgacag caacttcaaa gctgtgtctt accatgcctc tggccaaaat    660

gttgcctaca ggcctggagg ctttaaggcc agcactggct ttgggtccaa caccagaaac    720

aagaagatct acgatggggg tgcccgcaca gaagacgatg aacagtctca tcctaccaag    780

tatgactatg tgtag                                                     795
```

<210> SEQ ID NO 2
<211> LENGTH: 261
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 2

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140
```

```
Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 3
<211> LENGTH: 261
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 3

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240
```

```
Tyr Asp Gly Gly Ala Arg Thr Glu Asp Glu Val Gln Ser Tyr Pro Ser
                245                 250                 255

Lys His Asp Tyr Val
            260


<210> SEQ ID NO 4
<211> LENGTH: 247
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 4

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg
                245


<210> SEQ ID NO 5
<211> LENGTH: 741
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 5

caggtgcagc tgcaggagag cggccccggc ctgatcaagc ccagccagac cctgagcctg      60
```

-continued

```
acctgcaccg tgagcggcgg cagcatcagc agcggctaca actggcactg gatccggcag    120

ccccccggca agggcctgga gtggatcggc tacatccact acaccggcag caccaactac    180

aaccccgccc tgcggagccg ggtgaccatc agcgtggaca ccagcaagaa ccagttcagc    240

ctgaagctga gcagcgtgac cgccgccgac accgccatct actactgcgc ccggatctac    300

aacggcaaca gcttccccta ctggggccag ggcaccaccg tgaccgtgag cagcggtgga    360

ggcggttcag gcggaggtgg ttctggcggt ggcggatcgg acatcgtgat gacccagagc    420

cccgacagcc tggccgtgag cctgggcgag cgggccacca tcaactgcaa gagcagccag    480

agcctgttca acagcggcaa ccagaagaac tacctgacct ggtaccagca gaagcccggc    540

cagcccccca agctgctgat ctactgggcc agcacccggg agagcggcgt gcccgaccgg    600

ttcagcggca gcggcagcgg caccgacttc accctgacca tcagcagcct gcaggccgag    660

gacgtggccg tgtactactg ccagaacgcc tacagcttcc cctacacctt cggcggcggc    720

accaagctgg agatcaagcg g                                              741
```

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 6

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala
            20                  25
```

<210> SEQ ID NO 7
<211> LENGTH: 81
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 7

```
atggcctcac cgttgacccg ctttctgtcg ctgaacctgc tgctgctggg tgagtcgatt     60

atcctgggga gtggagaagc t                                               81
```

<210> SEQ ID NO 8
<211> LENGTH: 72
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 8

```
Thr Thr Thr Lys Pro Val Leu Arg Thr Pro Ser Pro Val His Pro Thr
1               5                   10                  15

Gly Thr Ser Gln Pro Gln Arg Pro Glu Asp Cys Arg Pro Arg Gly Ser
            20                  25                  30

Val Lys Gly Thr Gly Leu Asp Phe Ala Cys Asp Ile Tyr Ile Trp Ala
        35                  40                  45

Pro Leu Ala Gly Ile Cys Val Ala Leu Leu Leu Ser Leu Ile Ile Thr
    50                  55                  60
```

Leu Ile Cys Tyr His Arg Ser Arg
65 70

<210> SEQ ID NO 9
<211> LENGTH: 216
<212> TYPE: DNA
<213> ORGANISM: Artificial Sequence
<220> FEATURE:
<223> OTHER INFORMATION: Description of Artificial Sequence: artificially synthesized sequence

<400> SEQUENCE: 9
actactacca agccagtgct gcgaactccc tcacctgtgc accctaccgg gacatctcag 60
ccccagagac cagaagattg tcggccccgt ggctcagtga aggggaccgg attggacttc 120
gcctgtgata tttacatctg ggcacccttg gccggaatct gcgtggccct tctgctgtcc 180
ttgatcatca ctctcatctg ctaccacagg agccga 216

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 10

Lys Trp Ile Arg Lys Lys Phe Pro His Ile Phe Lys Gln Pro Phe Lys
1 5 10 15

Lys Thr Thr Gly Ala Ala Gln Glu Glu Asp Ala Cys Ser Cys Arg Cys
20 25 30

Pro Gln Glu Glu Glu Gly Gly Gly Gly Gly Tyr Glu Leu
35 40 45

<210> SEQ ID NO 11
<211> LENGTH: 135
<212> TYPE: DNA
<213> ORGANISM: Artificial Sequence
<220> FEATURE:
<223> OTHER INFORMATION: Description of Artificial Sequence: artificially synthesized sequence

<400> SEQUENCE: 11
aaatggatca ggaaaaaatt cccccacata ttcaagcaac catttaagaa gaccactgga 60
gcagctcaag aggaagatgc ttgtagctgc cgatgtccac aggaagaaga aggaggagga 120
ggaggctatg agctg 135

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 12

Ser Arg Ser Ala Glu Thr Ala Ala Asn Leu Gln Asp Pro Asn Gln Leu
1 5 10 15

Tyr Asn Glu Leu Asn Leu Gly Arg Arg Glu Glu Tyr Asp Val Leu Glu
20 25 30

Lys Lys Arg Ala Arg Asp Pro Glu Met Gly Gly Lys Gln Gln Arg Arg
35 40 45

-continued

```
Arg Asn Pro Gln Glu Gly Val Tyr Asn Ala Leu Gln Lys Asp Lys Met
    50                  55                  60

Ala Glu Ala Tyr Ser Glu Ile Gly Thr Lys Gly Glu Arg Arg Arg Gly
65                  70                  75                  80

Lys Gly His Asp Gly Leu Tyr Gln Gly Leu Ser Thr Ala Thr Lys Asp
                85                  90                  95

Thr Tyr Asp Ala Leu His Met Gln Thr Leu Ala
            100                 105
```

<210> SEQ ID NO 13
<211> LENGTH: 321
<212> TYPE: DNA
<213> ORGANISM: Artificial Sequence
<220> FEATURE:
<223> OTHER INFORMATION: Description of Artificial Sequence: artificially synthesized sequence

<400> SEQUENCE: 13

```
agcaggagtg cagagactgc tgccaacctg caggacccca accagctcta caatgagctc      60

aatctagggc gaagagagga atatgacgtc ttggagaaga agcgggctcg ggatccagag     120

atgggaggca aacagcagag gaggaggaac ccccaggaag gcgtatacaa tgcactgcag     180

aaagacaaga tggcagaagc ctacagtgag atcggcacaa aaggcgagag gcggagaggc     240

aaggggcacg atggccttta ccagggtctc agcactgcca ccaaggacac ctatgatgcc     300

ctgcatatgc agaccctggc c                                               321
```

<210> SEQ ID NO 14
<211> LENGTH: 247
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 14

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175
```

```
Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg
                245


<210> SEQ ID NO 15
<211> LENGTH: 242
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 15

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Gly Gly Tyr Arg Tyr Asp Glu Ala Met Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Ile Ser Tyr Met His Trp Tyr Gln Gln Lys Pro Gly Thr
                165                 170                 175

Ser Pro Lys Arg Trp Ile Tyr Asp Thr Ser Lys Leu Ala Ser Gly Val
            180                 185                 190

Pro Ala Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys His Gln
    210                 215                 220

Arg Ser Ser Tyr Pro Tyr Thr Phe Gly Gly Gly Thr Lys Leu Glu Ile
225                 230                 235                 240

Lys Arg


<210> SEQ ID NO 16
<211> LENGTH: 247
<212> TYPE: PRT
<213> ORGANISM: Artificial Sequence
<220> FEATURE:
```

<223> OTHER INFORMATION: Description of Artificial Sequence: artificially synthesized sequence

<400> SEQUENCE: 16

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Asn Thr Gly Glu Pro Thr Tyr Ala Glu Glu Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Ala Arg Phe Ser Tyr Gly Asn Ser Phe Ala Tyr Trp Gly Gln Gly Thr
100 105 110

Thr Val Thr Val Ser Ser Gly Gly Gly Gly Ser Gly Gly Gly Gly Ser
115 120 125

Gly Gly Gly Gly Ser Asp Ile Val Met Thr Gln Ser Pro Ser Ser Leu
130 135 140

Ser Val Ser Ala Gly Glu Lys Val Thr Met Ser Cys Lys Ser Ser Gln
145 150 155 160

Ser Leu Leu Asn Ser Gly Asn Gln Lys Asn Tyr Leu Ala Trp Tyr Gln
165 170 175

Gln Lys Pro Gly Gln Pro Pro Lys Leu Leu Ile Tyr Gly Ala Ser Thr
180 185 190

Arg Glu Ser Gly Val Pro Asp Arg Phe Thr Gly Ser Gly Ser Gly Thr
195 200 205

Asp Phe Thr Leu Thr Ile Ser Ser Val Gln Ala Glu Asp Leu Ala Val
210 215 220

Tyr Tyr Cys Gln Asn Asp His Ser Tyr Pro Leu Thr Phe Gly Ala Gly
225 230 235 240

Thr Lys Leu Glu Leu Lys Arg
245

<210> SEQ ID NO 17
<211> LENGTH: 247
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 17

Asp Val Gln Leu Gln Glu Ser Gly Pro Asp Leu Val Lys Pro Ser Gln
1 5 10 15

Ser Leu Ser Leu Thr Cys Thr Val Thr Gly Tyr Ser Ile Thr Ser Gly
20 25 30

Tyr Asn Trp His Trp Ile Arg Gln Phe Pro Gly Asn Lys Met Glu Trp
35 40 45

Met Gly Tyr Ile His Tyr Thr Gly Ser Thr Asn Tyr Asn Pro Ser Leu
50 55 60

Arg Ser Arg Ile Ser Ile Thr Arg Asp Thr Ser Lys Asn Gln Phe Phe
65 70 75 80

```
Leu Gln Leu Asn Ser Val Thr Thr Asp Asp Thr Ala Thr Tyr Tyr Cys
                85                  90                  95

Thr Arg Ile Tyr Asn Gly Asn Ser Phe Pro Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Pro Gly Glu Lys Val Thr Met Thr Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Arg Pro Gly Gln Pro Pro Lys Met Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Phe Tyr Cys Gln Asn Ala Tyr Ser Phe Pro Tyr Thr Phe Gly Gly Gly
225                 230                 235                 240

Thr Lys Leu Glu Ile Lys Arg
                245


<210> SEQ ID NO 18
<211> LENGTH: 247
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 18

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asp Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190
```

```
Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg
                245


<210> SEQ ID NO 19
<211> LENGTH: 247
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 19

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ala Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg
                245


<210> SEQ ID NO 20
<211> LENGTH: 247
<212> TYPE: PRT
<213> ORGANISM: Artificial Sequence
<220> FEATURE:
<223> OTHER INFORMATION: Description of Artificial Sequence:
```

artificially synthesized sequence

<400> SEQUENCE: 20

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ala Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg
                245
```

<210> SEQ ID NO 21
<211> LENGTH: 247
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg
                245


<210> SEQ ID NO 22
<211> LENGTH: 247
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190
```

```
Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg
                245
```

```
<210> SEQ ID NO 23
<211> LENGTH: 465
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 23

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Tyr Gly Ala Phe Asp Tyr Trp Gly Gln Gly Thr Thr Leu
            100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Gln Lys Phe Met Ser Thr
    130                 135                 140

Ser Val Gly Asp Arg Val Ser Ile Thr Cys Lys Ala Ser Gln Asn Val
145                 150                 155                 160

Arg Thr Ala Val Ala Trp Tyr Gln Gln Lys Pro Gly Gln Ser Pro Lys
                165                 170                 175

Ala Leu Ile Tyr Leu Ala Ser Asn Arg His Thr Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys Leu Gln His Trp Asn
    210                 215                 220

Tyr Pro Leu Thr Phe Gly Gly Gly Thr Lys Leu Glu Ile Lys Arg Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300
```

Ala Phe Ile Ile Phe Trp Val Arg Ser Lys Arg Ser Arg Leu Leu His
305 310 315 320

Ser Asp Tyr Met Asn Met Thr Pro Arg Arg Pro Gly Pro Thr Arg Lys
325 330 335

His Tyr Gln Pro Tyr Ala Pro Pro Arg Asp Phe Ala Ala Tyr Arg Ser
340 345 350

Arg Val Lys Phe Ser Arg Ser Ala Asp Ala Pro Ala Tyr Gln Gln Gly
355 360 365

Gln Asn Gln Leu Tyr Asn Glu Leu Asn Leu Gly Arg Arg Glu Glu Tyr
370 375 380

Asp Val Leu Asp Lys Arg Arg Gly Arg Asp Pro Glu Met Gly Gly Lys
385 390 395 400

Pro Gln Arg Arg Lys Asn Pro Gln Glu Gly Leu Tyr Asn Glu Leu Gln
405 410 415

Lys Asp Lys Met Ala Glu Ala Tyr Ser Glu Ile Gly Met Lys Gly Glu
420 425 430

Arg Arg Arg Gly Lys Gly His Asp Gly Leu Tyr Gln Gly Leu Ser Thr
435 440 445

Ala Thr Lys Asp Thr Tyr Asp Ala Leu His Met Gln Ala Leu Pro Pro
450 455 460

Arg
465

<210> SEQ ID NO 24
<211> LENGTH: 462
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 24

Gln Val Gln Leu Gln Gln Ser Gly Ala Glu Leu Ala Arg Pro Gly Ala
1 5 10 15

Ser Val Lys Leu Ser Cys Lys Ala Ser Gly Tyr Thr Phe Thr Asp Tyr
20 25 30

Tyr Ile Asn Trp Val Lys Gln Arg Thr Gly Gln Gly Leu Glu Trp Ile
35 40 45

Gly Glu Ile Tyr Pro Gly Ser Gly Asn Thr Tyr Tyr Asn Glu Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Ser Tyr Gly Ala Phe Asp Tyr Trp Gly Gln Gly Thr Thr Leu
100 105 110

Thr Val Ser Ser Gly Gly Gly Gly Ser Gly Gly Gly Gly Ser Gly Gly
115 120 125

Gly Gly Ser Asp Ile Val Met Thr Gln Ser Gln Lys Phe Met Ser Thr
130 135 140

Ser Val Gly Asp Arg Val Ser Ile Thr Cys Lys Ala Ser Gln Asn Val
145 150 155 160

Arg Thr Ala Val Ala Trp Tyr Gln Gln Lys Pro Gly Gln Ser Pro Lys
165 170 175

Ala Leu Ile Tyr Leu Ala Ser Asn Arg His Thr Gly Val Pro Asp Arg

```
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys Leu Gln His Trp Asn
    210                 215                 220

Tyr Pro Leu Thr Phe Gly Gly Gly Thr Lys Leu Glu Ile Lys Arg Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Ile Tyr Ile Trp
        275                 280                 285

Ala Pro Leu Ala Gly Thr Cys Gly Val Leu Leu Leu Ser Leu Val Ile
    290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
            340                 345                 350

Lys Phe Ser Arg Ser Ala Asp Ala Pro Ala Tyr Lys Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460


<210> SEQ ID NO 25
<211> LENGTH: 507
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 25

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80
```

```
Met Gln Leu Ser Ser Leu Thr Ser Glu Asp Ser Ala Val Tyr Phe Cys
                85                  90                  95

Ala Arg Ser Tyr Gly Ala Phe Asp Tyr Trp Gly Gln Gly Thr Thr Leu
            100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Gln Lys Phe Met Ser Thr
    130                 135                 140

Ser Val Gly Asp Arg Val Ser Ile Thr Cys Lys Ala Ser Gln Asn Val
145                 150                 155                 160

Arg Thr Ala Val Ala Trp Tyr Gln Gln Lys Pro Gly Gln Ser Pro Lys
                165                 170                 175

Ala Leu Ile Tyr Leu Ala Ser Asn Arg His Thr Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys Leu Gln His Trp Asn
    210                 215                 220

Tyr Pro Leu Thr Phe Gly Gly Gly Thr Lys Leu Glu Ile Lys Arg Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
    370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Gln Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg
```

500 505

<210> SEQ ID NO 26
<211> LENGTH: 473
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 26

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350
```

```
Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470


<210> SEQ ID NO 27
<211> LENGTH: 470
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 27

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240
```

```
Thr Lys Leu Glu Leu Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470
```

<210> SEQ ID NO 28
<211> LENGTH: 515
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 28

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser Gly Gly Gly Gly Ser Gly Gly Gly Gly Ser
```

```
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 29
```

```
<211> LENGTH: 472
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 29

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Phe Trp Val Leu Val Val Val Gly Gly Val Leu Ala Cys
    290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Arg Val Lys Phe Ser Arg Ser Ala Asp
        355                 360                 365

Ala Pro Ala Tyr Gln Gln Gly Gln Asn Gln Leu Tyr Asn Glu Leu Asn
```

```
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Gln Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470


<210> SEQ ID NO 30
<211> LENGTH: 469
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 30

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Thr Thr Thr Pro Ala Pro Arg Pro Pro Thr
                245                 250                 255
```

```
Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
            340                 345                 350

Gly Gly Cys Glu Leu Arg Val Lys Phe Ser Arg Ser Ala Asp Ala Pro
        355                 360                 365

Ala Tyr Lys Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465


<210> SEQ ID NO 31
<211> LENGTH: 514
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 31

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140
```

```
Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Phe Trp Val Leu Val Val Val Gly Gly Val Leu Ala Cys
    290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Lys Arg Gly Arg Lys Lys Leu Leu Tyr
        355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Gln Arg Arg Lys Asn Pro Gln Glu Gly Leu Tyr Asn Glu Leu
    450                 455                 460

Gln Lys Asp Lys Met Ala Glu Ala Tyr Ser Glu Ile Gly Met Lys Gly
465                 470                 475                 480

Glu Arg Arg Arg Gly Lys Gly His Asp Gly Leu Tyr Gln Gly Leu Ser
                485                 490                 495

Thr Ala Thr Lys Asp Thr Tyr Asp Ala Leu His Met Gln Ala Leu Pro
            500                 505                 510

Pro Arg


<210> SEQ ID NO 32
<211> LENGTH: 473
<212> TYPE: PRT
<213> ORGANISM: Artificial Sequence
<220> FEATURE:
<223> OTHER INFORMATION: Description of Artificial Sequence:
```

artificially synthesized sequence

<400> SEQUENCE: 32

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ala Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400
```

```
Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470


<210> SEQ ID NO 33
<211> LENGTH: 470
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 33

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ala Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285
```

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Lys Arg Gly Arg
305 310 315 320

Lys Lys Leu Leu Tyr Ile Phe Lys Gln Pro Phe Met Arg Pro Val Gln
325 330 335

Thr Thr Gln Glu Glu Asp Gly Cys Ser Cys Arg Phe Pro Glu Glu Glu
340 345 350

Glu Gly Gly Cys Glu Leu Arg Val Lys Phe Ser Arg Ser Ala Asp Ala
355 360 365

Pro Ala Tyr Lys Gln Gly Gln Asn Gln Leu Tyr Asn Glu Leu Asn Leu
370 375 380

Gly Arg Arg Glu Glu Tyr Asp Val Leu Asp Lys Arg Arg Gly Arg Asp
385 390 395 400

Pro Glu Met Gly Gly Lys Pro Arg Arg Lys Asn Pro Gln Glu Gly Leu
405 410 415

Tyr Asn Glu Leu Gln Lys Asp Lys Met Ala Glu Ala Tyr Ser Glu Ile
420 425 430

Gly Met Lys Gly Glu Arg Arg Arg Gly Lys Gly His Asp Gly Leu Tyr
435 440 445

Gln Gly Leu Ser Thr Ala Thr Lys Asp Thr Tyr Asp Ala Leu His Met
450 455 460

Gln Ala Leu Pro Pro Arg
465 470

<210> SEQ ID NO 34
<211> LENGTH: 515
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 34

Gln Val Gln Leu Gln Gln Ser Gly Ala Glu Leu Ala Arg Pro Gly Ala
1 5 10 15

Ser Val Lys Met Ser Cys Lys Ala Ser Gly Tyr Thr Phe Thr Ser Tyr
20 25 30

Thr Met His Trp Val Lys Gln Arg Pro Gly Gln Gly Leu Glu Trp Ile
35 40 45

Gly Tyr Ile Asn Pro Ala Ser Gly Tyr Thr Asn Tyr Asn Gln Lys Phe
50 55 60

Lys Asp Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Ile Tyr Tyr Gly Asn Ser Phe Ala Tyr Trp Gly Gln Gly Thr
100 105 110

Thr Val Thr Val Ser Ser Gly Gly Gly Gly Ser Gly Gly Gly Gly Ser
115 120 125

Gly Gly Gly Gly Ser Asp Ile Val Met Thr Gln Ser Pro Ser Ser Leu
130 135 140

Thr Val Thr Ala Gly Glu Lys Val Thr Met Ser Cys Lys Ser Ser Gln
145 150 155 160

Ser Leu Leu Asn Ser Gly Asn Gln Lys Asn Tyr Leu Thr Trp Tyr Gln

```
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515


<210> SEQ ID NO 35
<211> LENGTH: 473
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 35
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
```

```
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470


<210> SEQ ID NO 36
<211> LENGTH: 470
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300
```

```
Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 37
<211> LENGTH: 515
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190
```

```
Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515


<210> SEQ ID NO 38
<211> LENGTH: 473
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
```

```
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445
```

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470

<210> SEQ ID NO 39
<211> LENGTH: 470
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 39

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln

```
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 40
<211> LENGTH: 515
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 40

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205
```

```
Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515
```

<210> SEQ ID NO 41
<211> LENGTH: 473
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 41

```
Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45
```

```
Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460
```

Leu His Met Gln Ala Leu Pro Pro Arg
465 470

<210> SEQ ID NO 42
<211> LENGTH: 470
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 42

Gln Val Gln Leu Gln Glu Ser Gly Pro Gly Leu Ile Lys Pro Ser Gln
1 5 10 15

Thr Leu Ser Leu Thr Cys Thr Val Ser Gly Gly Ser Ile Ser Ser Gly
20 25 30

Tyr Asn Trp His Trp Ile Arg Gln Pro Pro Gly Lys Gly Leu Glu Trp
35 40 45

Ile Gly Tyr Ile His Tyr Thr Gly Ser Thr Asn Tyr Asn Pro Ala Leu
50 55 60

Arg Ser Arg Val Thr Ile Ser Val Asp Thr Ser Lys Asn Gln Phe Ser
65 70 75 80

Leu Lys Leu Ser Ser Val Thr Ala Ala Asp Thr Ala Ile Tyr Tyr Cys
85 90 95

Ala Arg Ile Tyr Asn Gly Asn Ser Phe Pro Tyr Trp Gly Gln Gly Thr
100 105 110

Thr Val Thr Val Ser Ser Gly Gly Gly Gly Ser Gly Gly Gly Gly Ser
115 120 125

Gly Gly Gly Gly Ser Asp Ile Val Met Thr Gln Ser Pro Asp Ser Leu
130 135 140

Ala Val Ser Leu Gly Glu Arg Ala Thr Ile Asn Cys Lys Ser Ser Gln
145 150 155 160

Ser Leu Phe Asn Ser Gly Asn Gln Lys Asn Tyr Leu Thr Trp Tyr Gln
165 170 175

Gln Lys Pro Gly Gln Pro Pro Lys Leu Leu Ile Tyr Trp Ala Ser Thr
180 185 190

Arg Glu Ser Gly Val Pro Asp Arg Phe Ser Gly Ser Gly Ser Gly Thr
195 200 205

Asp Phe Thr Leu Thr Ile Ser Ser Leu Gln Ala Glu Asp Val Ala Val
210 215 220

Tyr Tyr Cys Gln Asn Ala Tyr Ser Phe Pro Tyr Thr Phe Gly Gly Gly
225 230 235 240

Thr Lys Leu Glu Ile Lys Arg Thr Thr Thr Pro Ala Pro Arg Pro Pro
245 250 255

Thr Pro Ala Pro Thr Ile Ala Ser Gln Pro Leu Ser Leu Arg Pro Glu
260 265 270

Ala Cys Arg Pro Ala Ala Gly Gly Ala Val His Thr Arg Gly Leu Asp
275 280 285

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Lys Arg Gly Arg
305 310 315 320

Lys Lys Leu Leu Tyr Ile Phe Lys Gln Pro Phe Met Arg Pro Val Gln
325 330 335

Thr Thr Gln Glu Glu Asp Gly Cys Ser Cys Arg Phe Pro Glu Glu Glu
340 345 350

```
Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 43
<211> LENGTH: 515
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 43

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
```

```
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515


<210> SEQ ID NO 44
<211> LENGTH: 471
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 44

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60
```

-continued

```
Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Lys Pro Val Leu Arg Thr
                245                 250                 255

Pro Ser Pro Val His Pro Thr Gly Thr Ser Gln Pro Gln Arg Pro Glu
            260                 265                 270

Asp Cys Arg Pro Arg Gly Ser Val Lys Gly Thr Gly Leu Asp Phe Ala
        275                 280                 285

Cys Asp Ile Tyr Ile Trp Ala Pro Leu Ala Gly Ile Cys Val Ala Leu
    290                 295                 300

Leu Leu Ser Leu Ile Ile Thr Leu Ile Cys Tyr His Arg Ser Arg Lys
305                 310                 315                 320

Trp Ile Arg Lys Lys Phe Pro His Ile Phe Lys Gln Pro Phe Lys Lys
                325                 330                 335

Thr Thr Gly Ala Ala Gln Glu Glu Asp Ala Cys Ser Cys Arg Cys Pro
            340                 345                 350

Gln Glu Glu Glu Gly Gly Gly Gly Gly Tyr Glu Leu Ser Arg Ser Ala
        355                 360                 365

Glu Thr Ala Ala Asn Leu Gln Asp Pro Asn Gln Leu Tyr Asn Glu Leu
    370                 375                 380

Asn Leu Gly Arg Arg Glu Glu Tyr Asp Val Leu Glu Lys Lys Arg Ala
385                 390                 395                 400

Arg Asp Pro Glu Met Gly Gly Lys Gln Gln Arg Arg Arg Asn Pro Gln
                405                 410                 415

Glu Gly Val Tyr Asn Ala Leu Gln Lys Asp Lys Met Ala Glu Ala Tyr
            420                 425                 430

Ser Glu Ile Gly Thr Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Thr Leu Ala
465                 470
```